US009814395B2

(12) United States Patent
Stahmann et al.

(10) Patent No.: US 9,814,395 B2
(45) Date of Patent: Nov. 14, 2017

(54) METHOD AND APPARATUS FOR DETERMINATION OF PHYSIOLOGICAL PARAMETERS USING CERVICAL IMPEDANCE

(75) Inventors: Jeffrey E. Stahmann, Ramsey, MN (US); David J. Ternes, Roseville, MN (US); Barun Maskara, Blaine, MN (US); Shantha Arcot-Krishnamurthy, Vadnais Heights, MN (US); Juan Gabriel Hincapie Ordonez, Maple Grove, MN (US); Scott Vanderlinde, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 909 days.

(21) Appl. No.: 13/568,887

(22) Filed: Aug. 7, 2012

(65) Prior Publication Data
US 2013/0041269 A1 Feb. 14, 2013

Related U.S. Application Data

(60) Provisional application No. 61/522,047, filed on Aug. 10, 2011.

(51) Int. Cl.
*A61B 5/02* (2006.01)
*A61B 5/00* (2006.01)
(Continued)

(52) U.S. Cl.
CPC .......... *A61B 5/02007* (2013.01); *A61B 5/021* (2013.01); *A61B 5/0215* (2013.01);
(Continued)

(58) Field of Classification Search
CPC . A61B 5/02007; A61B 5/7203; A61B 5/4836; A61B 5/6877; A61B 5/021;
(Continued)

(56) References Cited

U.S. PATENT DOCUMENTS 4,425,920 A 1/1984 Bourland et al.
5,707,400 A * 1/1998 Terry, Jr. ............ A61N 1/36117
607/44
(Continued)

FOREIGN PATENT DOCUMENTS

JP 09187521 A 7/1997
JP 2004526471 A 9/2004
(Continued)

OTHER PUBLICATIONS

Bergel, D H, "The Static Elastic Properties of the Arterial Wall", J. Physiol (1961), 156, 445-457.
(Continued)

*Primary Examiner* — Tiffany Weston
*Assistant Examiner* — Tho Tran
(74) *Attorney, Agent, or Firm* — Schwegman Lundberg & Woessner, P.A.

(57) ABSTRACT

Implanted electrodes can be used to deliver electrical stimulation signals to areas near blood vessels, nerves, or other internal body locations. In an example, an electrode can be implanted in a cervical location and can be used to measure dimensional changes in an artery using impedance plethysmography. Measured artery dimensional changes can be used to determine one or more physiological parameters associated with a patient's health status, such as pulse transit time, relative pulse pressure, or aterial compliance, among others. These parameters can be used to monitor a patient health status or to modulate a patient's therapy, among other uses. In some examples, an electrode configured to deliver an electrostimulation signal to nerve tissue can be used to provide non-neurostimulating electrical stimulation plethysmography signals near a blood vessel.

20 Claims, 14 Drawing Sheets

(51) Int. Cl.
  *A61B 5/021* (2006.01)
  *A61B 5/0215* (2006.01)
  *A61B 5/0295* (2006.01)
  *A61B 5/053* (2006.01)
  *A61B 5/107* (2006.01)

(52) U.S. Cl.
  CPC .......... *A61B 5/0295* (2013.01); *A61B 5/0535* (2013.01); *A61B 5/1076* (2013.01); *A61B 5/4836* (2013.01); *A61B 5/686* (2013.01); *A61B 5/6876* (2013.01); *A61B 5/6877* (2013.01); *A61B 5/7203* (2013.01); *A61B 5/7275* (2013.01)

(58) Field of Classification Search
  CPC ... A61B 5/0535; A61B 5/1076; A61B 5/6876; A61B 5/0295; A61B 5/0215; A61B 5/686; A61B 5/7275
  See application file for complete search history.

(56) References Cited

U.S. PATENT DOCUMENTS

| | | | |
|---|---|---|---|
| 5,732,710 A | 3/1998 | Rabinovich et al. | |
| 6,540,699 B1 | 4/2003 | Smith | |
| 6,648,828 B2 | 11/2003 | Friedman et al. | |
| 7,542,800 B2 | 6/2009 | Libbus et al. | |
| 7,783,349 B2 | 8/2010 | Libbus et al. | |
| 7,873,413 B2 | 1/2011 | McCabe et al. | |
| 7,894,895 B2 | 2/2011 | Libbus et al. | |
| 2008/0147140 A1 | 6/2008 | Ternes et al. | |
| 2008/0194996 A1* | 8/2008 | Kassab | A61B 5/053 600/593 |
| 2009/0187110 A1 | 7/2009 | Voss et al. | |
| 2009/0306524 A1 | 12/2009 | Muhlsteff et al. | |
| 2010/0312128 A1 | 12/2010 | Karst et al. | |
| 2011/0009754 A1 | 1/2011 | Wenzel et al. | |
| 2011/0009927 A1 | 1/2011 | Parker et al. | |
| 2011/0015702 A1 | 1/2011 | Ternes et al. | |
| 2011/0087115 A1 | 4/2011 | Sackner et al. | |
| 2011/0224520 A1* | 9/2011 | Skerl et al. | 600/345 |
| 2012/0065527 A1 | 3/2012 | Gill et al. | |
| 2012/0172742 A1* | 7/2012 | Arcot-Krishnamurthy | A61B 5/0538 600/536 |
| 2012/0265296 A1* | 10/2012 | McNamara et al. | 623/2.17 |

FOREIGN PATENT DOCUMENTS

| | | | |
|---|---|---|---|
| JP | 2005185575 A | 7/2005 | |
| JP | 2005519680 A | 7/2005 | |
| JP | 2009538634 A | 11/2009 | |
| JP | 2010505465 A | 2/2010 | |
| JP | 2010516383 A | 5/2010 | |
| JP | 2011507667 A | 3/2011 | |
| JP | 2014522713 A | 9/2014 | |
| WO | WO-2008015598 | 2/2008 | |
| WO | WO-2008103077 A1 | 8/2008 | |
| WO | WO 2009/086536 A1 * | 7/2009 | A61B 5/042 |
| WO | WO-2013022886 A1 | 2/2013 | |

OTHER PUBLICATIONS

Grassi, Guido, et al., "Sympathetic Modulation of Radial Artery Compliance in Congestive Heart Failure", Hypertension. 1995; 26:348-354 http://hyper.ahajournals.org/content/26I2/348.long, 9 pgs.

Hayes, J, et al., "The relationship between vascular expansion of the aorta and pulmonary artery and the genesis of the impedance cardiogram using the technique of sonomicrometry", J Med Eng Technol Nov.-Dec. 2007;31:419-427, (2007), 419-427.

Kounalakis, S N, et al., "The Role of Pulse Transit Time as an Index of Arterial Stiffness During Exercise", Cardiovasc Eng (2009) 9:92-97, (2009), 92-97.

Smith, Robin P, et al., "Pulse transit time: an appraisal of potential clinical applications", Thorax 1999; 54:452-458, 452-458.

Tozzi, P, et al., "Cross-sectional compliance overestimates arterial compliance because it neglects the axial strain", Swiss Med Wkly 2003;133:461-464 http://www.sonometrics.com/Papers%5Ctozzi.vonsegesser03.pdf, (2003), 461-464.

"International Application Serial No. PCT/US2012/049851, International Preliminary Report on Patentability dated Feb. 20, 2014", 10 pgs.

"International Application Serial No. PCT/US2012/049851, International Search Report dated Jan. 30, 2013", 5 pgs.

"International Application Serial No. PCT/US2012/049851, Written Opinion dated Jan. 2013", 8 pgs.

"Japanese Application Serial No. 2014-525094, Office Action dated Jan. 6, 2015", With English Translation, 7 pgs.

* cited by examiner

METHOD AND APPARATUS FOR DETERMINATION OF PHYSIOLOGICAL PARAMETERS USING CERVICAL IMPEDANCE

CLAIM OF PRIORITY

This application claims the benefit of priority under 35 U.S.C. §119(e) of Stahmann et al., U.S. Provisional Patent Application Ser. No. 61/522,047, entitled "METHOD AND APPARATUS FOR DETERMINATION OF PHYSIOLOGICAL PARAMETERS USING CERVICAL IMPEDANCE", filed on Aug. 10, 2010, which is herein incorporated by reference in its entirety.

BACKGROUND

A medical device can be implanted in a body to perform one or more tasks including monitoring, detecting, or sensing physiological information in or otherwise associated with the body, diagnosing a physiological condition or disease, treating or providing a therapy for a physiological condition or disease, or restoring or otherwise altering the function of an organ or a tissue. Examples of an implantable medical device can include a cardiac rhythm management device, such as a pacemaker, a cardiac resynchronization therapy device, a neural stimulation device, a neuromuscular stimulator, or a drug delivery system, among others.

Neural stimulation or monitoring devices can be configured to deliver therapeutic pulse signals to nerve tissue to evoke a patient response, such as a cardiac response. The sympathetic and parasympathetic nervous systems can be modulated using neural stimulation, such as to protect against cardiac remodeling or predisposition to fatal arrhythmias after a myocardial infarction. In an example, neural stimulation can include autonomic modulation therapies (AMT) comprising stimulating neural targets in the autonomic nervous system, such as to treat disorders where autonomic imbalance can occur, such as in heart failure.

In an example, a medical device can be configured to monitor one or more patient physiological parameters, such as thoracic impedance, pulse transit time, relative pulse pressure, or changes in blood vessel geometry. In one example, Friedman et al., in U.S. Pat. No. 6,648,828, entitled "CONTINUOUS NON-INVASIVE TECHNIQUE FOR MEASURING BLOOD PRESSURE USING IMPEDANCE PLETHYSMOGRAPHY," refers to using impedance plethysmography to measure the impedance at two locations on a limb of an animal to detect when a blood pressure pulse occurs at those two locations. Impedance plethysmography can include applying an electrical current to body tissue and monitoring changes in voltage, an example, voltage changes can correspond with changes in body fluid volume.

In another example, Hayes et al., in Vol. 31, No. 6, November/December 2007, of the Journal of Medical Engineering and Technology, entitled "THE RELATIONSHIP BETWEEN VASCULAR EXPANSION OF THE AORTA AND PULMONARY ARTERY AND THE GENESIS OF THE IMPEDANCE CARDIOGRAM USING THE TECHNIQUE OF SONOMICROMETRY," refers to using impedance electrodes placed around a canine aorta to determine a contribution of vascular expansion of the aorta on an impedance cardiogram. Sonomicrometry can include applying ugh frequency vibrational energy ultrasound) to body tissue. For example, piezoelectric transducers, such as disposed in or on body tissue, can be used as ultrasound transmitters and receivers. The distance between the transducers can be determined by analyzing a propagation time of the ultrasound signal.

Pulse transit time and relative pulse pressure can be determined using various sensors disposed in or on a patient body to indicate, among other things, cardiac output or blood vessel compliance. For example, Kounalakis et al., in Vol. 9, August, 2009, of Cardiovascular Engineering, entitled "THE ROLE OF PULSE TRANSIT TIME AS AN INDEX OF ARTERIAL STIFFNESS DURING EXERCISE," notes that pulse transit time, as an index of functional vessel stiffness, can be affected by changes in cardiac output.

Implanted electrodes can be used to deliver electrical stimulation signals to areas near blood vessels, nerves, or other internal body locations. In an example, an electrode implanted in a cervical region (e.g., at or near a neck region) can be used to measure dimensional changes in an artery using impedance plethysmography. Measured artery dimensional changes can be used to determine one or more physiological parameters associated with a patient health status, such as pulse transit time, relative pulse pressure, or arterial compliance, among others. These parameters can be used to monitor a patient health status or to modulate a patient's therapy, among other uses. In an example, an electrode configured to deliver an electrostimulation signal to nerve tissue can be used to provide non-neurostimulating electrical stimulation plethysmography signals near a blood vessel.

The present inventors have recognized, among other things, that a problem to be solved can include monitoring a patient health status using impedance measurements to monitor relative pulse pressure or pulse transit time, among other physiological indicators. In an example, the present subject matter can provide a solution to this problem, such as by using plethysmography analysis techniques to process impedance information received from cervical body locations. In an example, the present subject matter can include using impedance plethysmography information to discern cervical blood vessel dimensional changes.

The present inventors have recognized, among other things, that another problem to be solved can include reducing a stimulation energy delivery frequency, such as to prolong battery life in an implantable device, or to reduce the number of energy deliveries provided to a patient body. In an example, the present subject matter can provide a solution to this problem, such as by incorporating impedance plethysmography pulse signals with neural stimulation pulse signals.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
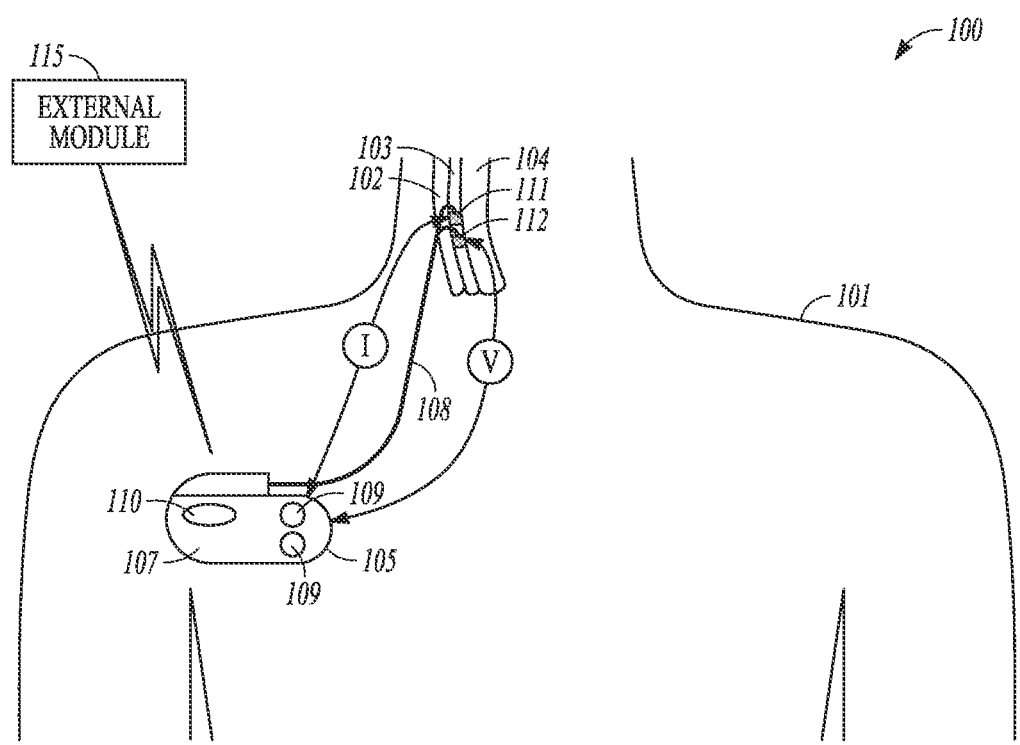
FIG. 1 illustrates generally an example that can include an ambulatory medical device and an external module.

FIG. 1 illustrates generally an example of a system 100, including an ambulatory or implantable medical device (IMD) 105 that can be placed subcutaneously or submuscularly in a subject body 101. In an example, the IMD 105 can include, among other components, one or more of a stimulating circuit 121 or a sensing circuit 122 (not shown in FIG. 1), such as can be configured to interact with muscle or nerve tissue in the subject body 101. The IMD 105 can further include a conductive housing 107 or a processor circuit 110 that can be coupled to one or more of the stimulating or sensing circuits or other components. In an example, a functional portion of one or more of the stimulating circuit 121, sensing circuit 122, or the processor circuit 110 can reside in the IMD 105, and another portion elsewhere (e.g., in an external programmer or analyzer circuit). In an example, the sensing circuit 122 can be used to detect one or more physiological parameters or responses, such as including blood pressure, cardiac activity parameters such as heart rate, and respiration parameters such as tidal volume and minute ventilation. The stimulating circuit 121 can be used to apply electrical stimulation pulses to muscle or nerve tissue in the subject body 101.

In an example, the IMD 105 can include a communication circuit and antenna, or telemetry coil, such as can be used to communicate wirelessly with an external module 115 or other device. The system 100 can include one or more leadless ECG electrodes 109 or other electrodes such as can be disposed on the housing of the Imp 105. These electrodes can be used to detect heart rate or cardiac arrhythmias, among other features of a cardiac cycle.

The external module 115 can include a remote medical device programmer or one or more other remote external modules (e.g., outside of wireless communication range of the IMD 105 antenna, but coupled to the IMD 105 using an external device, such as a repeater or network access point). The external module 115 can include a processor circuit 110 configured to process information that can be sent to or received from the IMD 105. The information can include medical device programming information, subject data, device data, or other instructions, alerts, or other information. In an example, the external module 115 can be configured to display information (e.g., received information) to a user. Further, the local programmer or the remote programmer can be configured to communicate the sent or received information to a user or physician, such as by sending an alert (e.g., via e-mail) of the status of the subject 101 or the system 100.

The IMD 105 can include a neurostimulation therapy device configured to provide therapeutic neural stimulation (NS) signals such as for delivery to one or more specified neural targets. In an example, the IMD 105 can include a cardiac rhythm management (CRM) device, such as a pacemaker, or a defibrillator, among other implantable medical devices. Such implantable devices can include a neural stimulation component and a cardiac rhythm management component. Generally, the processor circuit 110 can include a combination of hardware and software to perform the INS and CRM functions. For example, the therapeutic or diagnostic applications discussed in this disclosure can be stored as processor-readable instructions that are executable by the processor. The CRM component can include elements under the control of the processor to stimulate ahead or sense cardiac signals, such as using one or more electrodes disposed on or in the subject body 101. The NS component can include elements under the control of the processor to stimulate a neural stimulation target or sense parameters associated with nerve activity or surrogates of nerve activity, such as blood pressure and respiration.

In an example, such as shown in FIG. 1, the IMD 105 can be coupled to an implantable lead system 108. The implantable lead system 108 can include at least one neural stimulation lead that can be subcutaneously located such as for being tunneled to a neural target, such as in a cervical region (e.g., a region at or near the neck) in the subject body 101. A first electrode 111 can be disposed at the end of the lead, such as a first nerve cuff electrode. In an example, the first electrode 111 can include a nerve cuff electrode that can be sized, shaped, or otherwise configured to be disposed around a vagus nerve 103. Some other vagus nerve stimulation examples can include one or more electrodes that can be sized, shaped, or otherwise configured to be fed into a vessel near the vagus nerve 103, such as for using electrodes positioned within the vessel to intravascularly stimulate the neural target. For example, the vagus nerve 103 can be stimulated using electrodes positioned internally within a jugular vein 102 or a carotid artery 104.

Other examples can include delivering neural stimulation from within the trachea, or within a blood vessel in close proximity to a nerve, such as within the internal jugular vein, the superior vena cava, or the azygous, brachiocephalic, or the subclavian veins. In some cases, a neural target can be stimulated using ultrasound or light energy. One or more other neural targets, such as baroreceptors, cardiac nerves, and cardiac fat pads can additionally or alternatively be stimulated. In an example, the system 100 can include one or more satellite electrodes that can be positioned to stimulate a neural target. The satellite electrodes can be coupled to the IMD 105 using a wireless link, such as to provide stimulation and communication signals.

Figure 2:
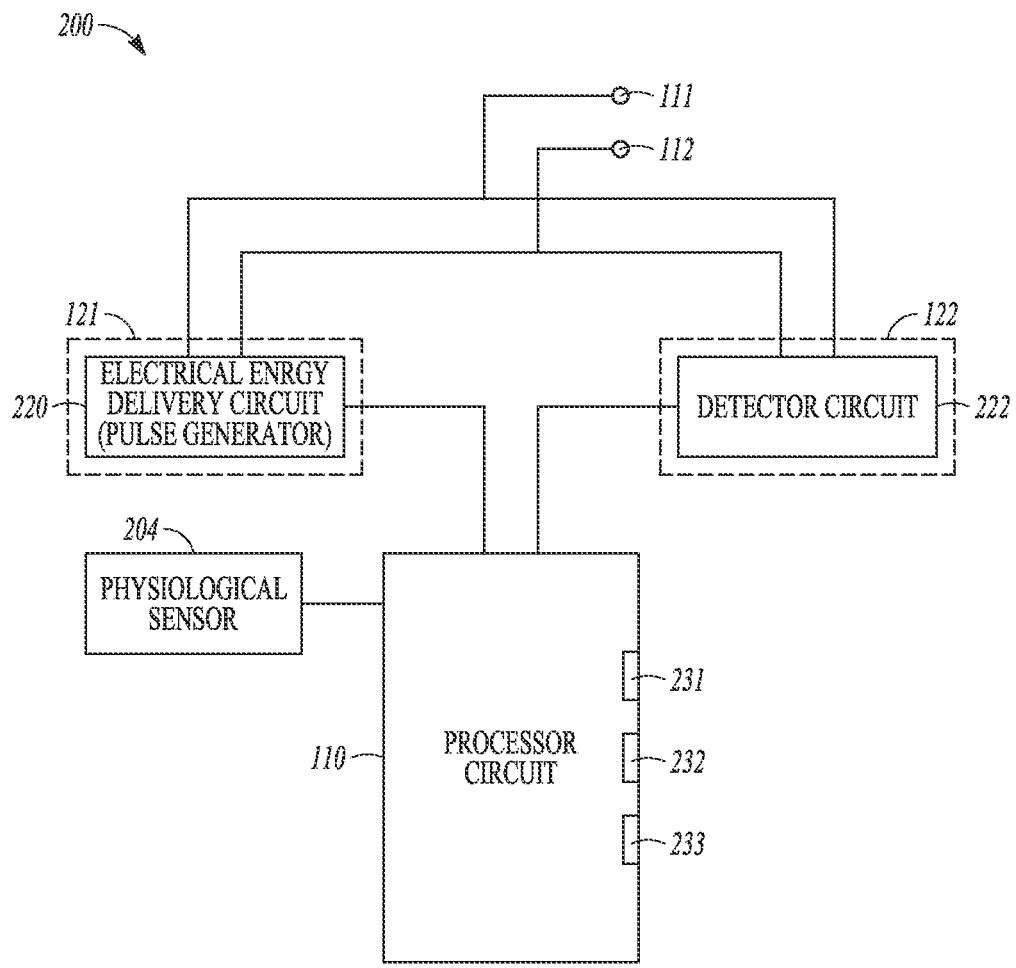
FIG. 2 illustrates generally an example that can include a processor circuit, an energy delivery circuit, and a detector circuit.

FIG. 2 illustrates generally an example of a system 200 that can comprise a portion of the system 100, such as including the IMD 105 and one or more electrode leads. The processor circuit 110 can include multiple data inputs or outputs 231, 232, or 233. Other data inputs or outputs of the processor circuit 110 can be coupled to a physiological sensor 204, a detector circuit 222, or an electrical energy delivery circuit 220, or another circuit or device. The physiological sensor 204 can include a posture sensor, a heart rate sensor, a respiration rate sensor, a respiratory phase sensor, a patient physical activity level sensor, an accelerometer, or a cardiac arrhythmia sensor, or another type of sensor. The sensor can be configured to provide a signal indicative of a patient physiological parameter or indicative of a change in a patient physiological parameter to the processor circuit 110 such as for interpretation or further processing.

In an example, the electrical energy delivery circuit 220 can be a subcomponent of the stimulating circuit 121. The electrical energy delivery circuit 220 can comprise a pulse generator that can be coupled to one or more electrodes (e.g., the first electrode 111 or the second electrode 112), such as including an implantable cuff electrode. The electrical energy delivery circuit 220 can be configured to generate current pulses and provide the pulses to the one or more electrodes, such as in response to a control signal provided by the processor circuit 110, such as after receiving a trigger signal from the physiological sensor 204.

The detector circuit 222 can be a subcomponent of the sensing circuit 122. The detector circuit 222, in conjunction with the processor circuit 110, can be configured to receive electrical signals from one or more electrodes, such as the first electrode 111 or the second electrode 112. In an example, the detector circuit 222 can be configured to measure a current, a voltage, or an impedance signal in or on the subject body 101. The signal can be received by the processor circuit 110 for further processing. In an example, the received signals can be passed from the processor circuit 110 to a different, second processor circuit, such as using the data output 231.

In an example, the electrical energy delivery circuit 220 can be configured to use a constant voltage source to deliver a current signal between two or more electrodes, such as can be disposed in a cervical body region. The detector circuit 222 can be configured to detect a responsive voltage signal using the same or different electrodes, such as can be disposed in the cervical body region. The responsive voltage signal can be analyzed using plethysmography techniques, such as to provide an indication of a change in a vessel dimension. One illustrative example of measuring an amount of fluid a subject body using a voltage source is described in Belalcazar et al., U.S. Pat. No. 7,640,056, entitled MONITORING FLUID IN A SUBJECT USING AN ELECTRODE CONFIGURATION PROVIDING NEGATIVE SENSITIVITY REGIONS, which is incorporated herein by reference in its entirety.

Figure 3A:
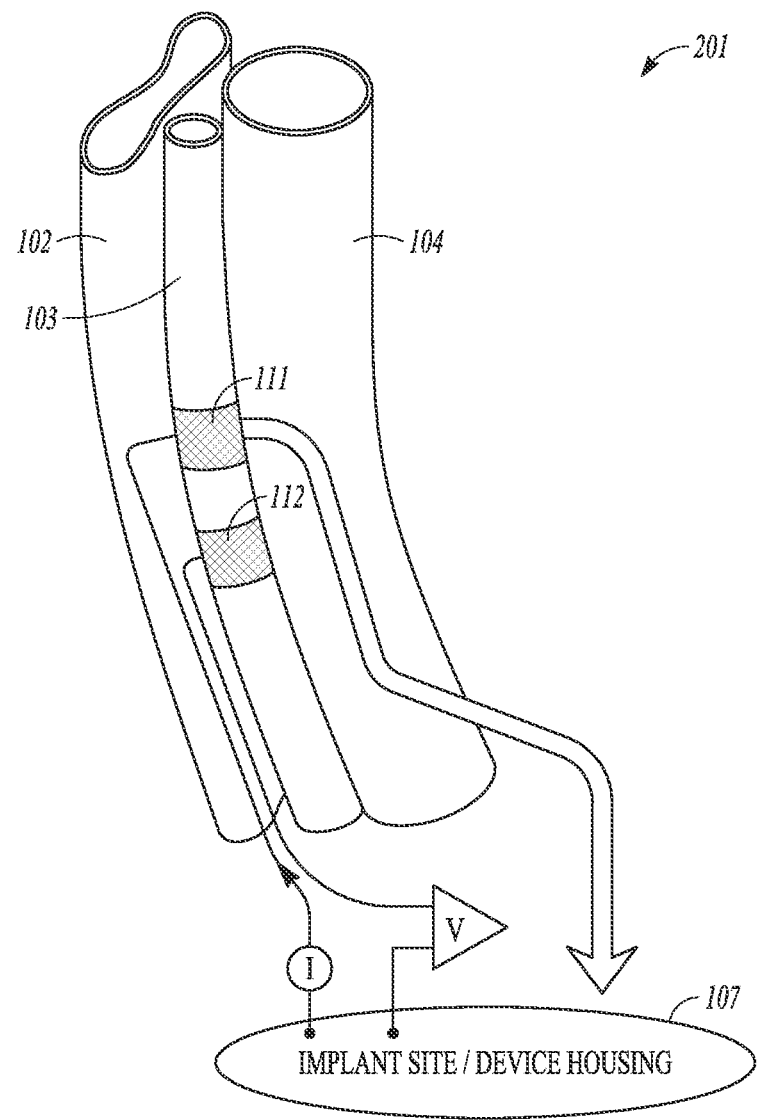
FIG. 3A illustrates generally an example that can include a unipolar energy de very system.
Figure 3B:
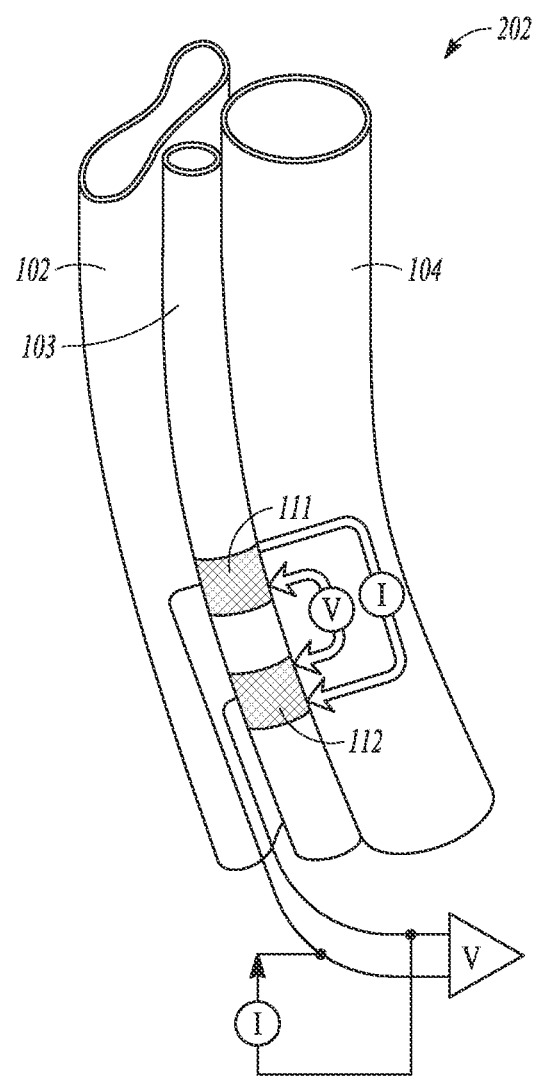
FIG. 3B illustrates generally an example that can include a bipolar energy de very system.

FIGS. 3A and 3B illustrate, respectively, examples of unipolar and bipolar measurement and therapy delivery configurations. These configurations can be used to acquire an impedance signal, such as using one or more electrodes disposed within the body (e.g., using the first and second electrodes 111, 112, such as disposed near a vagus nerve 103). An impedance signal can be used to measure one or more physiological parameters, which can be useful for managing or monitoring of, among other things, heart failure status or vagal stimulation therapy. In an example, an impedance signal can be used with one or more plethysmography techniques, such as to determine, among other things, pulsatile motion of a blood vessel, blood flow, blood pressure, or change in a blood vessel dimension, such as by monitoring a relatively small change in electrical resistance in a body.

In an example, impedance plethysmography can be used to determine a change in a dimension of an artery (e.g., the carotid artery 104), such as a change in a cross-sectional area or a radial dimension. An impedance signal for plethysmography analysis can be obtained using one or more electrodes that can be disposed in a cervical region of the patient body 101, such as using one or more cuff electrodes that can be disposed at or around the vagus nerve 103.

In an example, an impedance plethysmography signal can be received in response to a neural stimulation signal, such as can be delivered to the vagus nerve 103. For example, a neural stimulation signal can be used as a trigger for generating an impedance-measuring excitation signal. A response signal to the impedance-measuring excitation signal can be analyzed using plethysmography techniques. In an example, a neural stimulation signal can provide the excitation from which an impedance response can be measured.

FIG. 3A illustrates generally an example of a system 201 that can be configured to provide a unipolar electrical stimulation signal or to receive an electrical measurement signal, such as across a cervical or thoracic region in the subject body 101. In an example, the processor circuit 110 can initiate production of an electrical current pulse (e.g., an electrical current test pulse or an electrical current therapy pulse) in the IMD 105 using the stimulating circuit 121. The stimulating circuit 121 can be configured to deliver the current pulse, such as to a target cervical location (e.g., a neural stimulation target location proximate to the vagus nerve 103) using the first electrode 111. The sensing circuit 122 can be configured to receive a signal in response to the current pulse. Such a response signal can be measured using the same electrodes or one or more other electrodes, such as using the second electrode 112 and the conductive housing 107 of the IMD 105. In an example, the sensing circuit 122 can be configured to measure a thoracic impedance signal, such as using the unipolar configuration illustrated in the system 201.

FIG. 3B illustrates generally an example of a system 202 that can be configured to provide bipolar electrical stimulation signals or receive electrical measurement signals in a cervical region in the patient body 101, such as near the vagus nerve 103. In an example, the processor circuit 110 can initiate production of an electrical current pulse (e.g., an electrical current test pulse or therapy pulse) in the IMD 105 using the stimulating circuit 121. The stimulating circuit 121 can be configured to deliver the current pulse to a target cervical location using multiple electrodes disposed at or near the target location, such as using the first electrode 111 and the second electrode 112.

In an example, the first electrode 111 and the second electrode 112 can be electrodes disposed on a single implantable lead, such as a multipolar electrode lead comprising two or more electrodes. For example, the first electrode 111 and the second electrode 112 can be two of four electrodes on a quadripolar electrode lead. In an example, different electrodes can be used for delivering a current signal and measuring a corresponding, responsive voltage signal. One illustrative example of some electrode configurations for performing an impedance measurement is described in Stahmann et al., U.S. Pat. No. 7,387,610, entitled THORACIC IMPEDANCE DETECTION WITH BLOOD RESISTIVITY COMPENSATION, which is incorporated herein by reference in its entirety.

In an example, the processor circuit 110 can execute an electrode selection algorithm to select appropriate electrodes as the first electrode 111 and the second electrode 112 from among three or more available electrodes, such as can be disposed on any one or more implantable leads in the implantable lead system 108 or elsewhere. For example, the electrode selection algorithm can analyze one or more electrode selection parameters, such as impedance signal strength or repeatability, such as using available pairs of electrodes, which can then be used to select an electrode pair to use for impedance plethysmography measurement.

The sensing circuit 122 can be configured to receive a signal in response to the current pulse, such as can be measured using the same first electrode 111 and second electrode 112, or as can be measured using at least one other, different electrode, such as some combination of a third electrode and the conductive housing 107 of the IMD 105. The bipolar configuration of the system 202 can be used to generally provide a focused delivery of energy to a region in the subject body 101 (e.g., a cervical region). In an example, the bipolar configuration of the system 202 can be used to sense a response signal across a relatively narrow region of the subject body 101 (e.g., a cervical region). In an example, a bipolar configuration can require less energy than a unipolar configuration to evoke an electrostimulation response (e.g., an impedance-measurement response), such as capture of vagal tissue, because of the localization of energy delivery.

Figure 4:
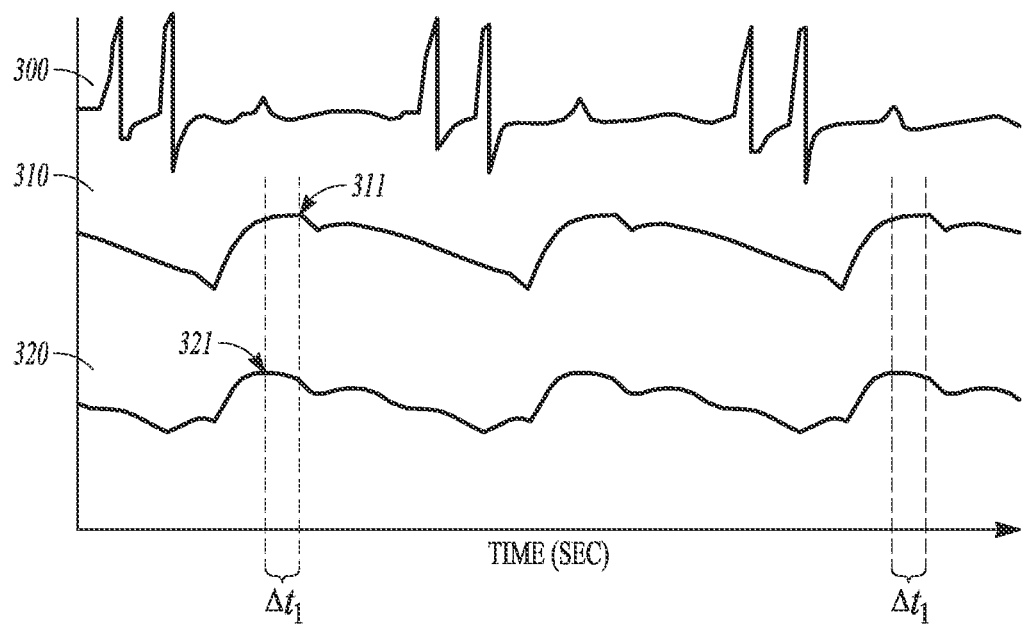
FIG. 4 illustrates generally an example of an ECG waveform and corresponding blood vessel expansion and impedance waveforms.
Figure 5:
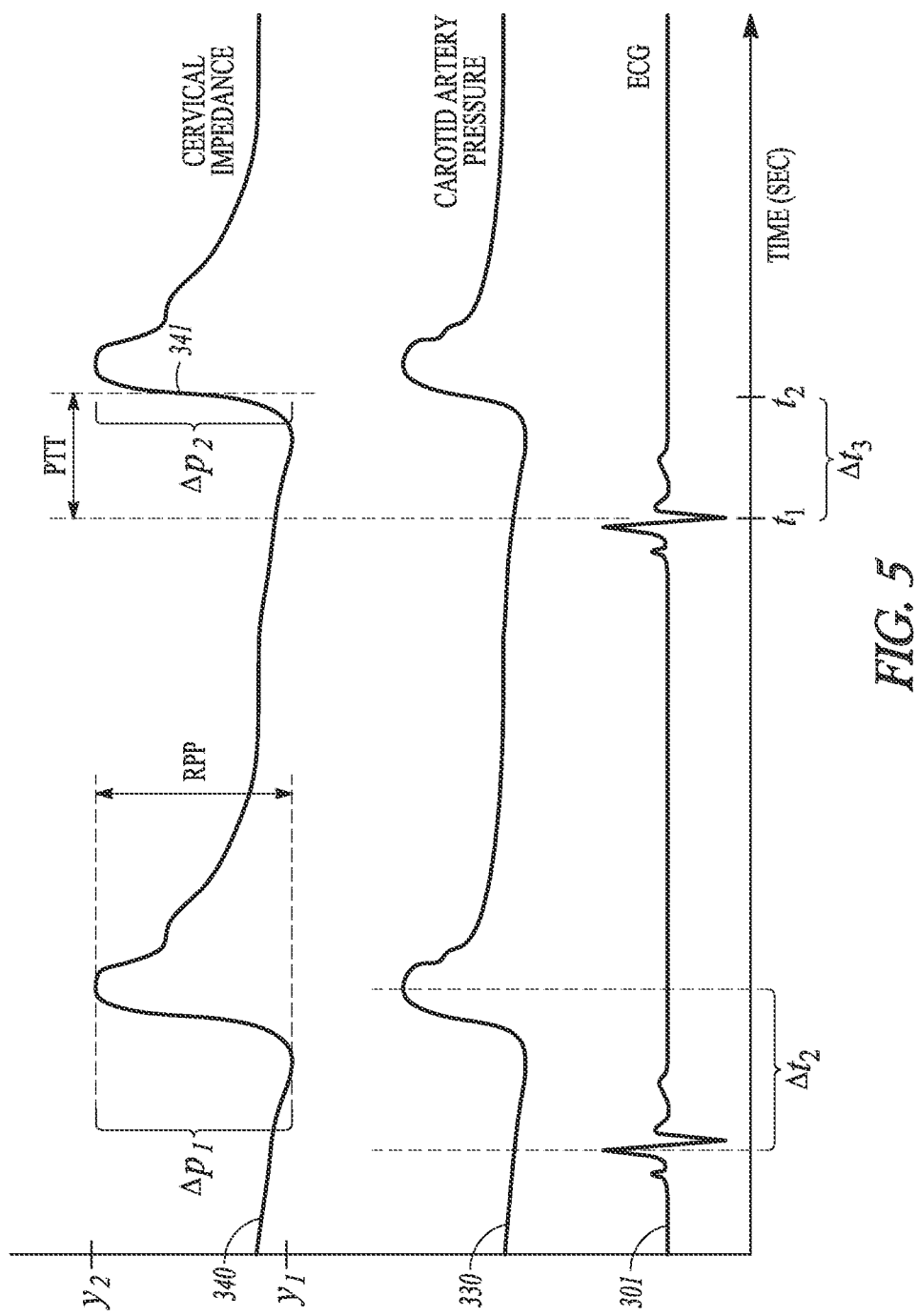
FIG. 5 illustrates generally an example of an ECG waveform and corresponding cervical impedance and blood vessel pressure waveforms.

FIGS. 4 and 5 illustrate generally examples of several waveforms that can be measured, such as using the system 100. The several waveform illustrations can have a common origin and time axis. In an example, such as shown in FIG. 4, an ECG waveform 300 can be obtained using at least two leadless ECG electrodes such as can be disposed on the housing of the MD 105. In an example, the ECG waveform 300 can be obtained using a device other than the IMD 105, such as an external monitoring device.

A blood vessel expansion signal 310 can be measured using, among other techniques, sonomicrometry or impedance plethysmography signals. The blood vessel expansion signal 310 can indicate, among other things, a relative change in a diameter or portion of a diameter of the blood vessel over one or more cardiac cycles. A corresponding blood vessel impedance signal 320 can be obtained. In an example, such as shown in FIG. 4, changes in blood vessel impedance can correspond with changes in blood vessel expansion. For example, a relative maximum impedance 321 over a first cardiac cycle can precede a corresponding relative maximum blood vessel expansion 311, such as by a time $\Delta t_1$. Subsequent relative maximum and minimum impedances can similarly correspond to relative maximum and minimum points of blood vessel expansion such that the blood vessel impedance signal 320 can be an effective surrogate for blood vessel expansion. In an example, information obtained from the blood vessel impedance signal 320 can be used to derive dimensional information about the vessel, including information about a change in the blood vessel dimension, such as to indicate the presence or passage of a blood pressure pulse.

The example of FIG. 5 illustrates a second ECG waveform 301. A carotid artery pressure signal 330, corresponding to the ECG waveform 301, is also shown, an example, a physiological blood pressure sensor can be disposed in or near the carotid artery 104 such as to provide the carotid artery pressure signal 330. Similarly to the example of FIG. 4, relative maxima and minima of the ECG signal 301 (e.g., the peak of the R wave or the minimum of the S wave) and the carotid artery pressure signal 330 are generally offset by a time of about $\Delta t_2$.

A cervical impedance signal 340 can be measured, such as using the configuration of the system 100, the system 201, or the system 202, among others. Cervical impedance can correspond with carotid artery pressure. For example, a maximum carotid artery pressure can correspond temporally with a maximum cervical impedance. That is, when a carotid artery pressure is at a maximum, the expansion of the artery can also be at a maximum. Consequently, impedance measurements, such as impedance plethysmography measurements, can indicate that a radial dimension of the artery is at a maximum, such as due to the elevated blood vessel pressure.

One or several physiological parameters, such as including pulse transit time (PIT) or relative pulse pressure (RPP), can be derived from the cervical impedance signal 340. Such physiological parameters can be used to provide information about patient physiological status, such as information about blood pressure, aterial compliance or stiffness, cardiac contractility, autonomic status, pulmonary vein distension, respiratory effort or disturbance (e.g., including apnea), or a patient fluid status, among other things. Such information can be used to monitor a patient status, to provide information for patient diagnostics, or to titrate a patient therapy, such as including a neurostimulation therapy.

In an example, arterial compliance or stiffness can be characterized by a ratio of change in blood pressure over change in a vessel dimension, such as a diameter, such as over one or more cardiac cycles. The cervical impedance signal can be used to obtain, substantially concurrently, a relative indication of a blood pressure in a vessel and a corresponding change in the vessel diameter.

In an example, such as shown in FIG. 5, a pulse transit time can be determined. The pulse transit time can be a time interval between a triggering event and a pulse receipt event (e.g., a blood pressure pulse) in a blood vessel. For example, a pulse transit time can be the time for an arterial pulse pressure wave to travel from a left ventricle of a heart to a peripheral body site, such as to the carotid artery.

In an example, a portion of the ECG signal 301 can be used as a reference to provide a PTT triggering event. The triggering event can include a cardiac event, such as corresponding to a particular portion of a QRS complex. The triggering event can include the occurrence of a heart sound, or a receipt of a pulse in a first location in a blood vessel, or an emptying of the left ventricle. In an example, such as shown in FIG. 5, the triggering event can occur at a time $t_1$, or the minimum amplitude of the QRS complex of a particular cardiac cycle of the ECG signal 301. The pulse receipt event can be an indication that a pulse or pressure wave has arrived at or passed through a blood vessel. For example, the pulse receipt event can include, among other things, a maximum arterial pressure, or a physical change in a vessel shape, such as can be detected using a light source and a photodetector, or using a change in a received impedance signal. In an example, such as shown in FIG. 5, the pulse receipt event can correspond to an inflection point 341 on the cervical impedance signal 340 waveform, such as at a time $t_2$. In this example, a pulse transit time can be represented by the interval $\Delta t_3$, or by the interval between $t_1$ and $t_2$.

Figure 6A:
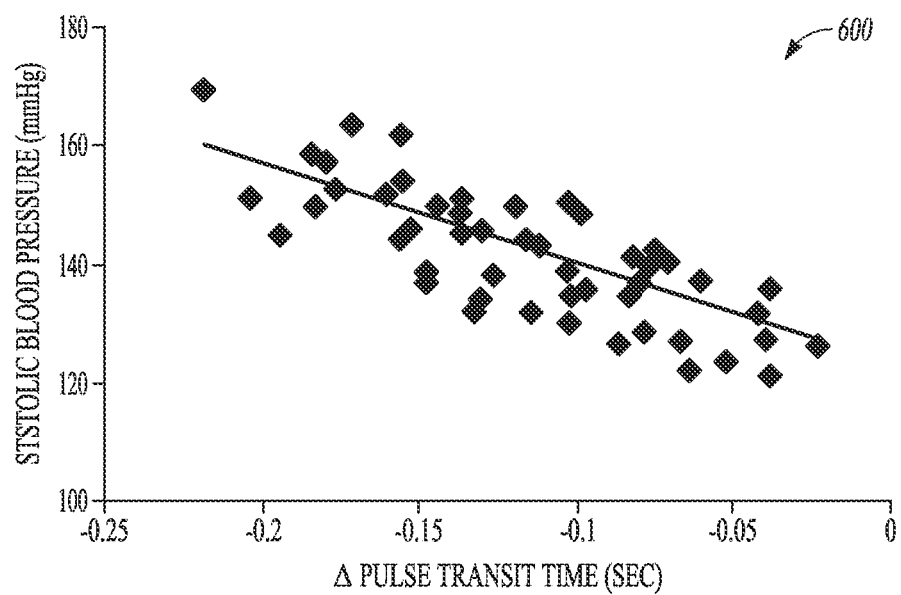
FIG. 6A illustrates generally a graphical representation of a relationship between a change in pulse transit time and blood pressure.

Pulse transit time, and particularly changes in pulse transit time, can be correlated with one or more physiological changes or changes in patient health status. Thus, monitoring pulse transit time can provide diagnostic information about a patient Or can indicate a patient therapy. For example, systolic blood pressure can be correlated with pulse transit time. In an example, such as shown in FIG. 6A, increasing pulse transit time can correspond generally with decreasing systolic blood pressure. This is believed to be because increased blood pressure can stretch blood vessel walls such that the walls can become less compliant, thus permitting increased blood flow velocity and decreased pulse transit time.

Figure 6B:
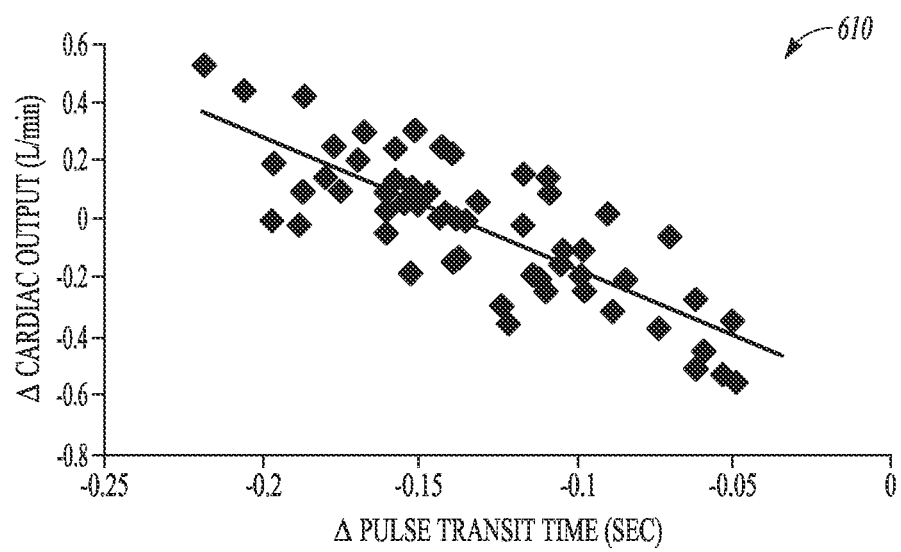
FIG. 6B illustrates generally a graphical representation of a relationship between a change in pulse transit time and cardiac output.

In another example, cardiac output can be correlated with pulse transit time. FIG. 6B illustrates generally that increasing pulse transit time can correspond generally with decreasing cardiac output. As cardiac output increases, arterial watts can be stretched and can become less compliant, corresponding to a decrease in pulse transit time.

Relative pulse pressure can be another useful parameter that can be determined using impedance plethysmography analysis techniques on impedance signals obtained in a cervical region of the subject body 101. A relative pulse pressure can be conceptualized as a difference between systolic and diastolic pressures, such as relative to prior measured pressure values. In an example, such as shown in FIG. 5, a first relative pulse pressure $\Delta p_1$ can be measured using the cervical impedance signal 340 as a surrogate for vessel pressure. Maxima and minima of the cervical impedance signal 340 can correspond to maxima and minima of a vessel pressure, such as corresponding to maximum systolic and minimum diastolic pressures. A second relative pulse pressure $\Delta p_2$ can be measured at a subsequent time. In an example, a change in relative pulse pressure from $\Delta p_1$ and $\Delta p_2$ (e.g., a difference between a first measured relative pulse pressure and a second measured relative pulse pressure) can indicate a change in a patient health status.

Impedance signals received from various body locations can be used to assess a patient health status, such as using impedance plethysmography analysis. In an example, impedance signals can be acquired from any location where electrodes are configured to deliver a neural stimulation therapy in proximity to a major or minor artery. Cervical locations, such as at or near the carotid artery or internal jugular vein, can be particularly useful because a carotid pulse can, in a healthy individual, be a strong, clear pulse sufficiently spaced away from the heart to provide useful and meaningful diagnostic parameters (e.g., relative pulse pressure or pulse transit time, among others). Non-cervical locations can be additionally or alternatively used. In an example, electrodes configured to deliver a kidney therapy can be disposed at or near a renal nerve and a renal artery, and can be used to acquire an impedance plethysmography signal. In an example, some electrodes configured to deliver a bladder therapy can be disposed at or near a sacral nerve and a sacral artery, and can be used to acquire an impedance plethysmography signal.

Impedance plethysmography response signals, such as can be received from electrodes disposed in cervical regions near an artery (e.g., a carotid artery or an internal jugular vein) to provide information about a change in an arterial dimension, can generally be received in response to an impedance plethysmography pulse signal applied to the cervical region. Impedance plethysmography pulse signals can generally be characterized as relatively low amplitude, non-tissue-stimulating (i.e., sub-capture threshold) pulses configured to provide a diagnostic measurement.

In an example, electrodes disposed in one or more cervical regions near an artery can include electrodes disposed on or near a vagus nerve. Such electrodes can be used to deliver neural stimulation pulses, such as to provide a therapeutic effect for the patient. For example, some cardiac antiarrhythmia therapies, among other therapies, can be delivered by applying electrical pulses to the vagus nerve.

In an example, some pulse signal characteristics can be common to impedance plethysmography pulse signals (e.g., non-neurostimulating signals) and neural stimulation pulse signals, such as vagus nerve stimulation (VNS) pulses. For example, both neurostimulating and non-neurostimulating signals can include at least some similar pulse features, such as amplitudes, pulse widths, or frequencies. This overlap in pulse signal characteristics, and an appropriate electrode location configuration, can enable dual use of the impedance plethysmography and neural stimulation pulse signals, such as to provide neural electrostimulation while acquiring an impedance plethysmography signal using the neural electrostimulation energy as an "excitation" or "test" signal for obtaining the impedance plethysmography information.

One or several benefits, such as including improved signal to noise performance and noise rejection, can be obtained by using neural stimulation pulse signals as test signals for impedance plethysmography measurements. In an example, neural stimulation pulse signals can generally be delivered at high current levels because neural stimulation pulse signals can be configured to deliver patient therapies at signal amplitudes exceeding a nerve tissue capture threshold. In contrast, signals used exclusively for impedance plethysmography can be delivered at relatively low current levels because these signals are not configured to stimulate tissue and evoke a response. In an example, the signals used for impedance plethysmography may necessarily (e.g., to avoid tissue capture) be too low to obtain a functional response signal. Thus, by using a higher amplitude neural stimulation pulse signal as at least a portion of the impedance plethysmography test pulse, a functional impedance response signal is more likely to be received, while concerns about tissue capture during impedance sensing can be eliminated.

Using relatively high amplitude therapy signal as the test signal for impedance plethysmography measurements can provide better resolution of the received measurement signals. For example, the signal to noise ratio of the test signal relative to background electrical noise can be improved. Because of the higher amplitude, there can be reduced susceptibility to interference, both internally to the subject body 101 and externally.

In an example, a therapy signal and an impedance plethysmography test signal can be combined. This can improve the longevity of a medical device, such as by reducing power consumption requirements by consolidating the number of individual pulses that are delivered to the subject body. In addition, by using neural stimulation signals as impedance plethysmography test signals, overall system design can be facilitated or other trade-offs can advantageously be made because there is little or no need to avoid collisions between neural stimulation and impedance plethysmography pulse signals.

Figure 7:
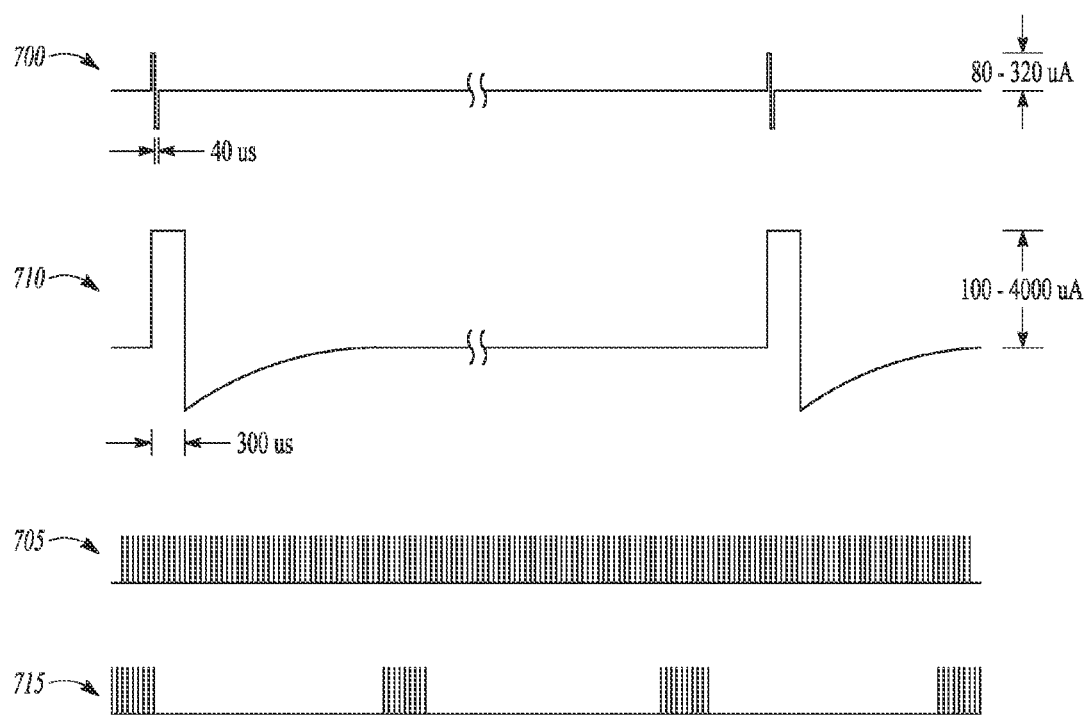
FIG. 7 illustrates generally an example that can include impedance plethysmography pulse signals and neural stimulation pulse signals.

FIG. 7 illustrates generally an impedance plethysmography pulse signal 700. This signal can be provided to the subject body 101, such as using the electrical energy delivery circuit 220 or the first electrode 111 disposed in a cervical region, such as to evoke an impedance response that can be used to provide information about a patient health status. In an example, the impedance plethysmography pulse signal 700 can be used to assess a patient respiration status (e.g., minute ventilation (MV) status), thoracic fluid status, or other physiological status. In an example, such as shown in FIG. 7, the impedance plethysmography pulse signal 700 can include a biphasic pulse signal having a duration of about 40 µs and a peak amplitude of about 80 to 320 µA. In an example, an MV test pulse, such as the impedance plethysmography pulse signal 700, can be delivered to the subject body 101 about every 50 ms such that an MV parameter can be continuously or recurrently sampled at about 20 Hz (see FIG. 7 at 705 for a graphical representation of continuous or recurrent, 20 Hz delivery of MV test pulses).

FIG. 7 also illustrates generally an example of a neural stimulation pulse signal 710. This signal can be provided to a cervical region of the subject body 101, such as at or near the vagus nerve 103, to deliver a neural stimulation therapy. The neural stimulation pulse signal 710 can include a biphasic pulse signal having a first, positive phase duration of about 300 µs at an amplitude of about 100-4000 µA. The neural stimulation pulse signal 710 can include a second, negative phase, such as immediately following the first phase and having an initial minimum magnitude less than zero. The second, negative phase can include a positively sloped portion, extending from the initial minimum, that is continuously or exponentially increasing toward zero. In an example, the neural stimulation pulse signal 710 can be delivered to the subject body 101 in burst fashion. For example, the pulse signal can be delivered discontinuously at about 20 Hz sampling rate such as by delivering the neural stimulation pulse signal 710 continuously for about 10 sec, pausing for about 50 sec, and resuming for another 10 sec. During the 10 sec that the pulse signal is applied, it can be applied at about 20 Hz. A graphical example of a delivery frequency of the neural stimulation pulses is illustrated graphically at 715.

Several techniques can be used to deliver neural stimulation pulse signals and impedance plethysmography pulse signals or receive impedance information, such as using the same electrodes. In an example, gaps between neural stimulation pulses (e.g., during an "off" or paused neural stimulation period) can be occupied using impedance plethysmography-only pulse signals. During these "off" portions of the neural stimulation pulse train, impedance plethysmography pulses (e.g., non-tissue-stimulating pulses) can be provided to the subject body 101 to obtain impedance measurements (e.g., to obtain a portion of the cervical impedance signal 340).

In an example, neural stimulation pulse signals or a signal delivery component can be modified to improve impedance measurements obtained in response to applying the neural stimulation pulse signals. For example, an electrode configuration can be modified, such as by using a unipolar configuration (see, e.g., FIG. 3A and the corresponding discussion) instead of a bipolar configuration (see, e.g., FIG. 3B and the corresponding discussion). In an example, a neural stimulation pulse configuration can be modified, such as by using a biphasic stimulation waveform instead of a monophasic waveform. In another example, a neural stimulation pulse configuration can be modified by changing a burst pulse train period from having an "on" portion and an "off" portion to a signal having a continuous "on" portion, yet maintaining the same number of pulses per period. For example, if a first configuration having a 60 second pulse train period delivers 20 pulses during a 10 second "on" portion, and delivers no pulses during a 50 second "off" portion, a second configuration can deliver 20 equally spaced apart pulses over the full 60 second pulse train period.

In an example, impedance measurements can be obtained, such as by sampling a voltage one or more times during delivery of a single, relatively long duration neural stimulation pulse. For example, the neural stimulation pulse signal 710 can have a duration of about 300 µs, and the impedance plethysmography pulse signal 700 can have a duration of about 40 µs. If impedance is to be sampled at least every 100 µs in response to the neural stimulation pulse signal 710, at least three impedance measurements can be obtained during delivery of the relatively long duration (e.g., 300 µs) of at least the first phase of the neural stimulation pulse signal 710.

Figure 8:
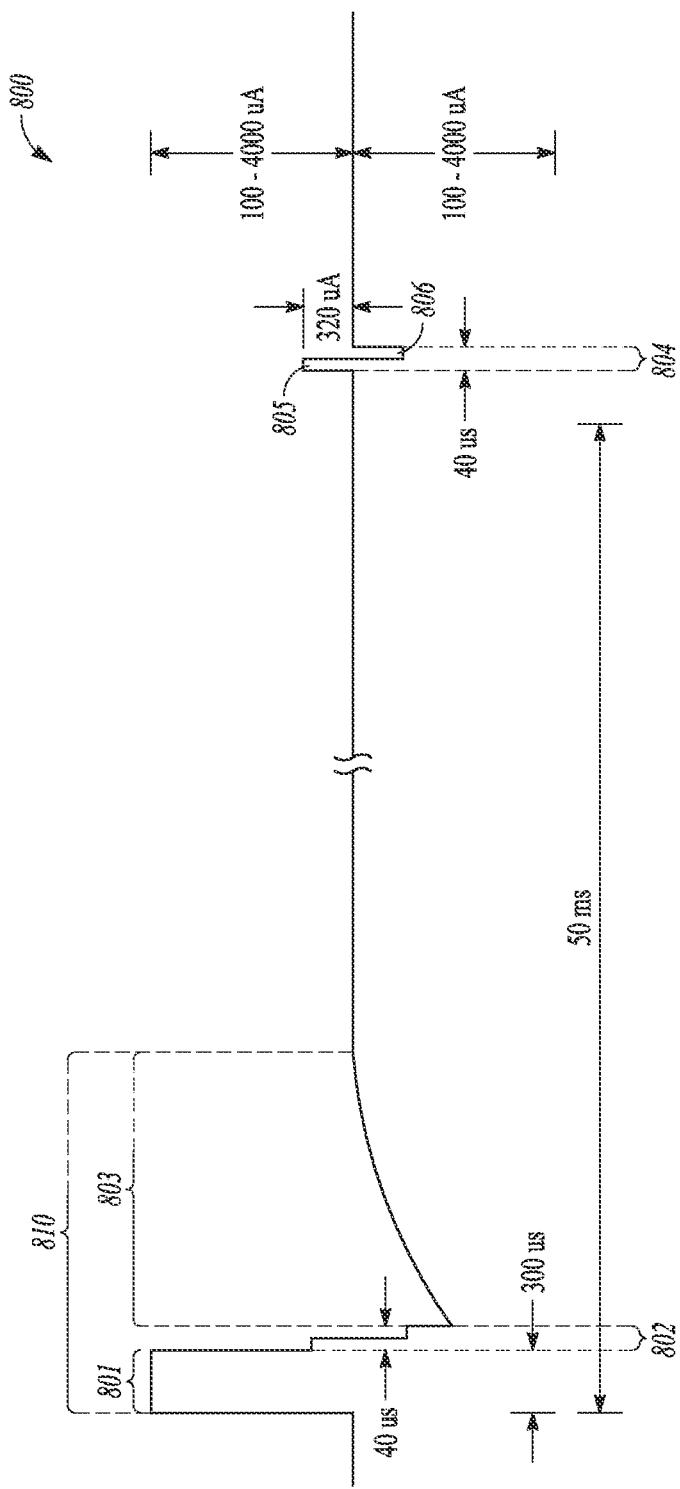
FIG. 8 illustrates generally an example that can include a waveform with impedance plethysmography signal components and neural stimulation signal components.

FIG. 8 illustrates generally an example that can include modifying a pulse waveform to include both neural stimulation and impedance plethysmography components. A waveform 800 can include at least a first composite pulse component 810 comprising a neural stimulation positive phase pulse component 801, an impedance plethysmography pulse component 802, and a neural stimulation negative phase pulse component 803. The waveform 800 can include a second pulse component 804, comprising positive and negative phases of an impedance plethysmography pulse, such as subsequent to the first composite pulse component 810.

In an example, such as shown in FIG. 8, an impedance plethysmography pulse signal (e.g., the impedance plethysmography pulse signal 700) can be appended to a trailing portion of the neural stimulation positive phase pulse component 801. In an example, the impedance plethysmography pulse signal 700 can be applied during periods of neural stimulation inactivity (e.g., between signal delivery bursts). This configuration can help provide consistent impedance plethysmography measurements at least because a consistent amplitude for the impedance plethysmography pulse signal 700 (e.g., about 320 µA peak) can be used regardless of an amplitude of the neural stimulation pulse signal 710.

Figure 9:
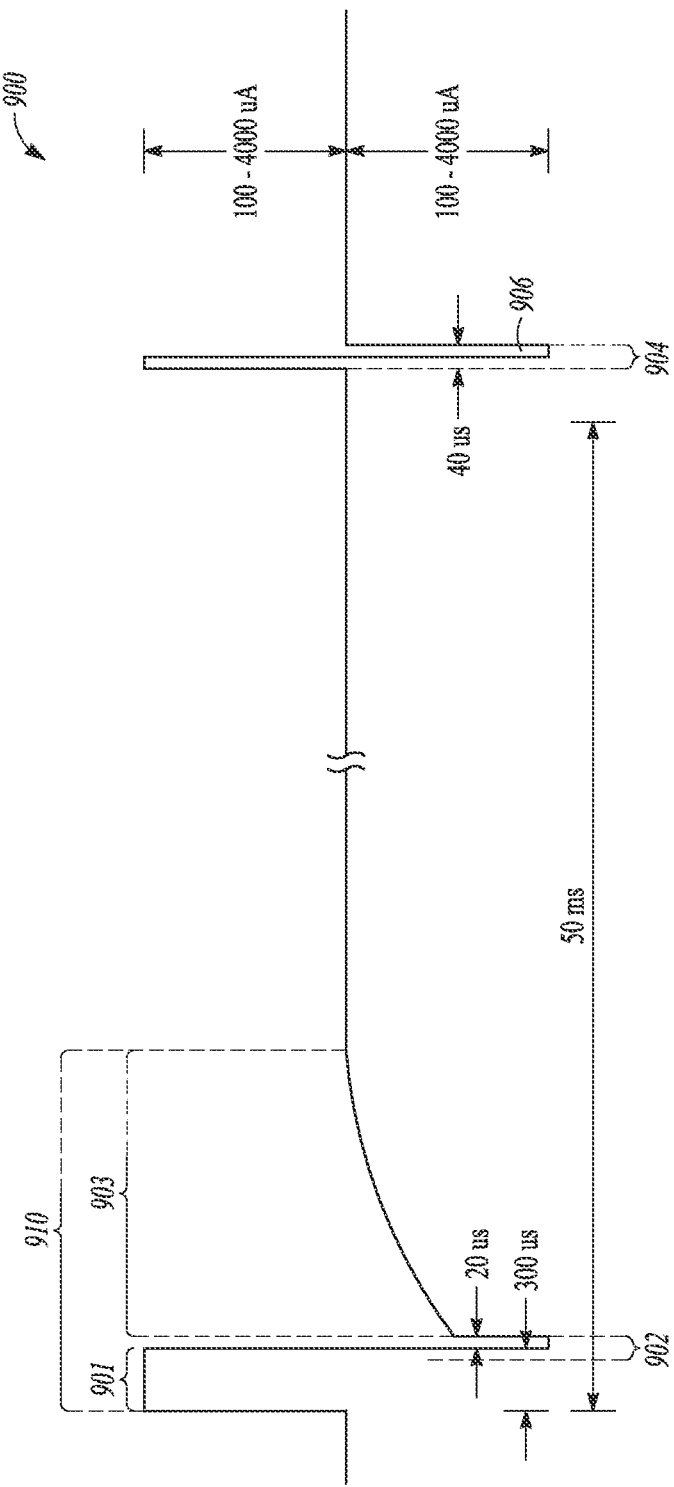
FIG. 9 illustrates generally an example that can include a waveform with impedance plethysmography signal components and neural stimulation signal components with passive recharge.

FIG. 9 illustrates generally an example that can include modifying a pulse waveform to include both neural stimulation and impedance plethysmography components. A waveform 900 can include at least a second composite pulse component 910 comprising a neural stimulation positive phase pulse component 901, an impedance plethysmography pulse component 902, and a neural stimulation negative phase pulse component 903. The waveform 900 can include a second pulse component 904 comprising positive and negative phases of an impedance plethysmography pulse, such as subsequent to the second composite pulse component 910.

In an example, such as shown in FIG. 9, an impedance plethysmography pulse signal can be incorporated with a trailing portion of the neural stimulation positive phase pulse component 901. Impedance plethysmography measurements can be received in response to the negative phase portion of the impedance plethysmography pulse component 903. In an example, a second impedance plethysmography pulse signal can be applied during periods of neural stimulation inactivity (e.g., between signal delivery bursts). Such second impedance plethysmography pulse signals can, for example, be delivered at the same amplitude as the neural stimulation pulse component 901. In an example, the pulse width of the second impedance plethysmography pulse signals (e.g., the second pulse component 904) can be reduced such that the signals are delivered below a nerve tissue capture threshold. In an example, the magnitude of the negative phase component 906 of the second impedance plethysmography pulse signal can be about the same as the negative phase component of the impedance plethysmography pulse component 902 that can be included in the second composite pulse component 910.

In an example, such as shown in FIG. 9, the impedance plethysmography pulse component 902 can reduce the time needed for passive recharge of the pulse delivery circuit (e.g., the electrical energy delivery circuit 220), such as by providing a trailing edge portion that is at a higher amplitude than would otherwise be used with an unaltered neural stimulation pulse. Consequently, impedance sensing can occur more rapidly after delivery of the neural stimulation pulse, and the impedance plethysmography sampling rate can be increased. In an example, the passive recharge time of the pulse delivery circuit can be reduced by including a negative phase, sub-capture threshold pulse component configured to dissipate any residual tissue charge that can accumulate during a positive phase pulse (e.g., a neural stimulation pulse).

Figure 10:
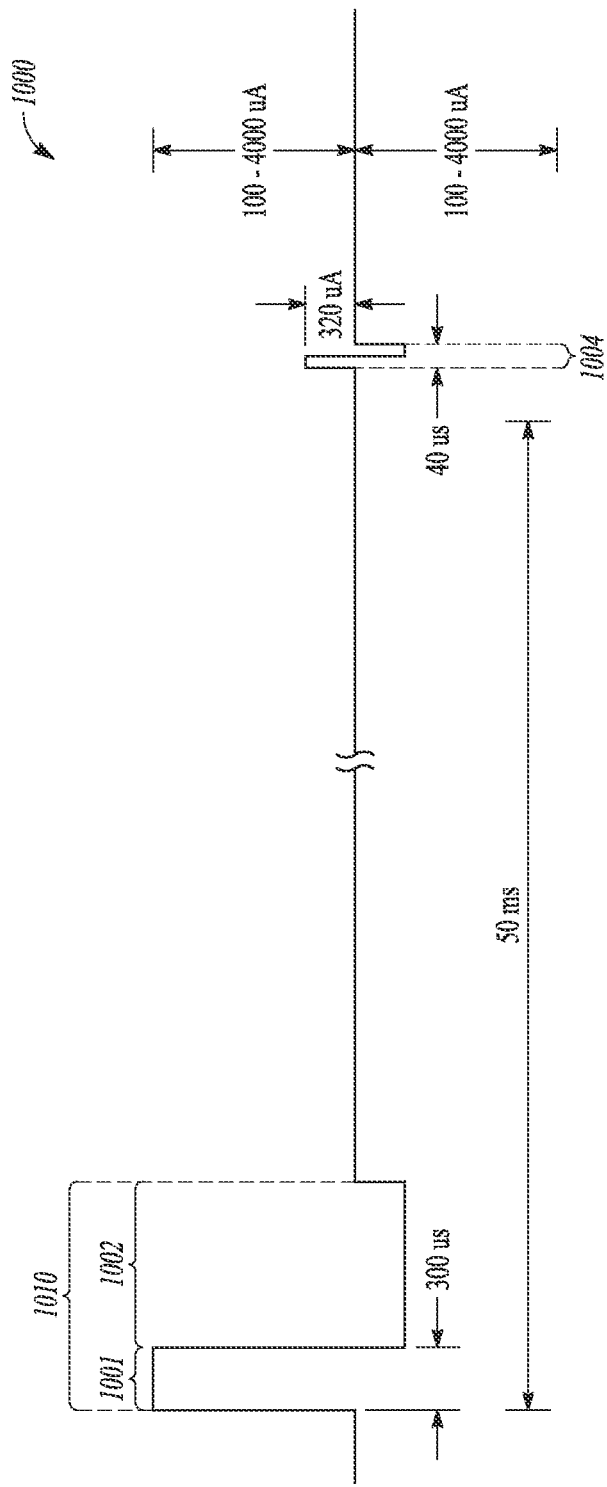
FIG. 10 illustrates generally an example that can include a charge balanced waveform with impedance plethysmography signal components and neural stimulation signal components.

FIG. 10 illustrates generally an example that can include a charge balanced waveform 1000 with active recharge. The waveform 1000 can include at least a charge balanced composite pulse component 1010 comprising a neural stimulation positive phase pulse component 1001, and a sub-capture threshold negative phase pulse component 1002. In an example, impedance plethysmography measurements can be obtained in response to the sub-capture threshold negative phase pulse component 1002. The duration of the negative phase component can be adjusted based on the requirements of the neural stimulation signal portion or a pulse width required to remain below a nerve or muscle tissue capture threshold.

Figure 11:
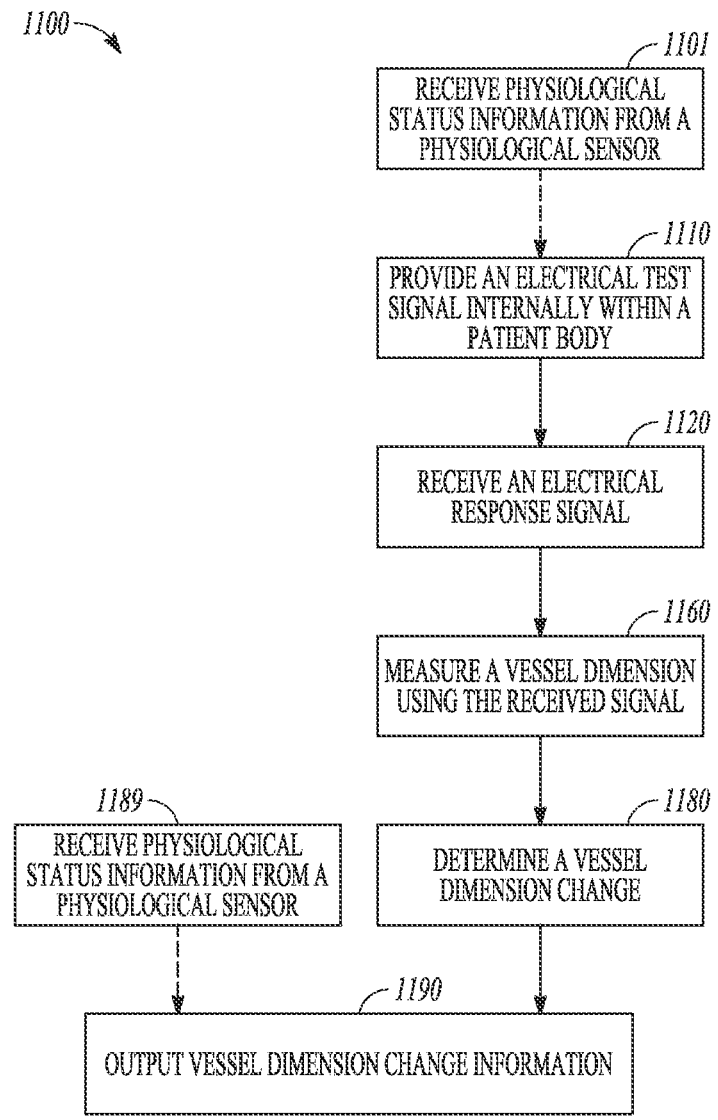
FIG. 11 illustrates generally an example that can include determining a vessel dimension change.

FIG. 11 illustrates generally an example that can include providing information about a vessel dimension. At 1110, an electrical test signal can be provided internally within a patient body, such as using one or more of the systems 100, 201, or 202, among others. For example, the electrical test signal can be a non-tissue stimulating (e.g., sub-capture threshold) signal, such as the impedance plethysmography pulse signal 700, that can be delivered using a bipolar electrode configuration. The electrical test signal can include a tissue stimulating signal, such as the neural stimulation pulse signal 710 configured to provide an autonomic modulation therapy to a patient nerve. In an example, the electrical test signal can be delivered to a cervical region within a subject body 101, such as at or near the vagus nerve 103 and proximal to the carotid artery 104.

At 1120, an electrical response signal can be received, such as using the detector circuit 222 or one or more of the data inputs or outputs 231, 232, or 233. The electrical response signal can be received in response to the electrical test signal provided at 1110. In an example, the electrical response signal can be an impedance plethysmography signal that can be processed, such as using the processor circuit 110, or stored using a processor-readable medium coupled to the processor circuit 110.

At 1160, a vessel dimension can be measured using the received signal, such as using a received impedance plethysmography signal. The vessel dimension can be measured by analyzing differences in received impedance signals, including differences in amplitude, phase, or other features of a received impedance signal in an example, the measured dimension can be a radial vessel dimension (e.g., a radial dimension of a carotid artery).

At 1180, a vessel dimension change can be measured. A vessel dimension change can, in an example, correspond to a change in the magnitude of a response signal received at 1120, such as a change in impedance magnitude. In an example, the vessel dimension change can be determined using the processor circuit 110 or the external module 115, such as by comparing the measured vessel dimension with a previously determined vessel dimension, a reference vessel dimension, or some other known value that can be used to provide relative vessel dimension change information.

In an example, the reference vessel dimension can be a standard or known dimension that can be provided to the processor circuit 110 or the external module 115. For example, the dimension can be preset by a clinician or other device programmer, such as using the external module 115. In an example, the reference vessel dimension can be a measured dimension, such as can be measured under a controlled or known patient physiological status. The dimension can be measured using plethysmography, imaging, or other techniques that can provide dimension information about a vessel.

In an example, the processor circuit 110 can be configured to determine the reference vessel dimension during a device learning period. The learning period can include multiple physiological cycles, such as corresponding to one or more patient physical activity levels. In an example, the reference vessel dimension can be obtained by averaging dimensional information obtained while a patient is at rest, such as over multiple cardiac cycles. The dimensional information can be measured at about the same time during or after a cardiac contraction, such as for each of the multiple cardiac cycles. For example, a carotid artery radial dimension can be repeatedly measured after a delay (e.g. a 100 ms delay) triggered by a portion of a patient ECG waveform (e.g., a peak amplitude portion). The radial dimension can be measured for multiple consecutive cycles (e.g., 10 cycles) and averaged, such as to determine a reference carotid artery radial dimension.

At 1190, information about the vessel dimension change can be provided, such as using the processor circuit 110. The information about the vessel dimension change can be provided to other portions of the IMD 105, such as to indicate a patient therapy is needed. Alternatively, or in addition, information about the vessel dimension change can be provided to the external module 115 for further processing or interpretation by another device or caregiver. In an example, the processor circuit 110 can determine or receive the information about the vessel dimension change and can calculate at least one of a relative pulse pressure or a pulse transit time.

A pulse transit time can be determined using information about a vessel dimension change, such as can be received by the processor circuit 110 at 1190. For example, the IMD 105 can obtain an indication of a cardiac event, such as using an ECG or heart sound signal. In an example, the information about a blood vessel dimensional change provided at 1190 can include timing information, such as information about when a blood vessel radial dimension exceeds some threshold dimension or reaches a maximum radial dimension. Using the indication of the cardiac event and the timing information about the blood vessel dimensional change, the processor circuit 110 can determine a pulse transit time.

In an example, such as shown in FIG. 11, information can be received by the processor circuit 110 from the physiological sensor 204, such as in response to a change in a patient physiological status. For example, the received information can indicate a change in a patient activity level, a patient posture change, a heart rate or respiratory rate change, or an arrhythmia status. At 1101, information about a patient physiological status can be received from the physiological sensor 204. Upon receipt of the information, the processor circuit 110 can initiate delivery of the electrical test signal at 1110. Similarly, at 1189, the processor circuit 110 can receive information from the same or different physiological sensor 204. In response to receiving the information, the processor circuit 110 can initiate a calculation or diagnostic procedure, or can communicate information about the blood vessel dimension change or other physiological parameter derived using impedance plethysmography measurements.

Figure 12:
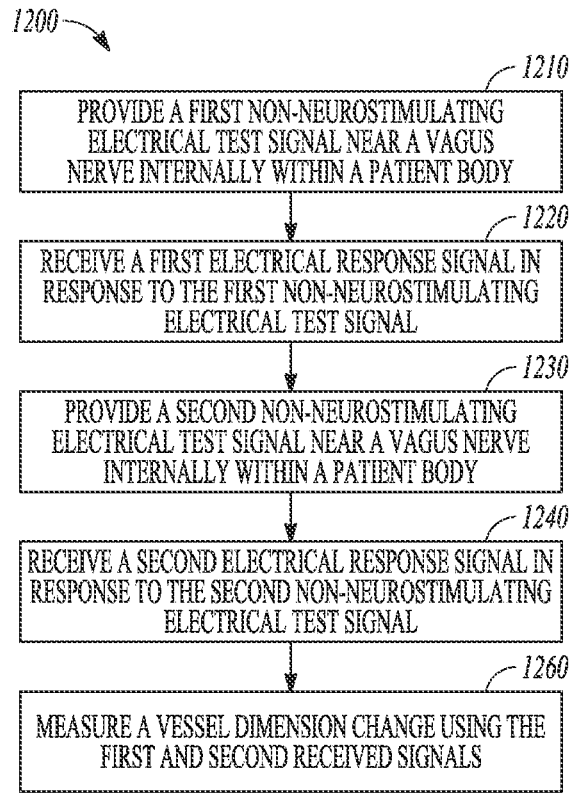
FIG. 12 illustrates generally an example that can include determining a vessel dimension change using multiple received response signals.

FIG. 12 illustrates generally an example that can include measuring a vessel dimension change using multiple received impedance signals. For example, at 1210, a first non-neurostimulating electrical test signal can be applied to the subject body 101, such as internally near the vagus nerve 103. The first non-neurostimulating electrical test signal can be the impedance plethysmography pulse signal 700, such as having an amplitude or pulse width below a neural tissue capture threshold. Providing the first non-neurostimulating electrical test signal at 1210 can be performed using any of the systems 100, 201, or 202, among others, such as using a pulse generator in the electrical energy deliver circuit 220.

At 1220, a first electrical response signal can be received, such as in response to the first non-neurostimulating electrical test signal provided at 1210. The first electrical response signal can be an impedance plethysmography response signal, such as can be used to determine a vessel dimension or a change in a vessel dimension. In an example, the first electrical response signal can be received using the detector circuit 222.

At 1230, a second non-neurostimulating electrical test signal can be applied to the subject body 101, such as internally near the vagus nerve 103. In an example, the second non-neurostimulating electrical test signal can be delivered using some or all of the same electrodes used to apply the first non-neurostimulating electrical test signal. At 1240, a second electrical response signal can be received, such as in response to the second non-neurostimulating electrical test signal. The second electrical response signal can be an impedance plethysmography response signal that can be used to determine a blood vessel dimension, such as a diameter.

At 1260, a vessel dimension change can be determined using the first and second received electrical response signals. For example, the first received electrical response signal can be used to obtain a first indication of a vessel dimension, such as a first radius. The second received electrical response signal can be used to obtain a second indication of a vessel dimension, such as a second radius. By comparing the first and second indications of the vessel dimension, a vessel dimension change can be determined.

In an example, the first and second non-neurostimulating electrical test signals provided at 1210 and 1230 can be provided sequentially, such as within a few milliseconds. In an example, the time between delivery of the first and second non-neurostimulating electrical test signals can be a larger interval. In an example, the first non-neurostimulating electrical test signal can be provided in response to a first indication of a patient physiological status, such as a first patient physical activity level, such can be obtained using an accelerometer the physiological sensor 204). The second non-neurostimulating electrical test signal can be provided in response to a second, different indication of a patient physiological status, such as a different second patient physical activity level, such as can be obtained using the same accelerometer. In an example, a patient blood vessel dimension change can be monitored over changes in a patient physiological status, such as to indicate a patient health status. In an example, blood vessel dimension changes can be monitored over longer periods of time, such as using trends or histograms, to better determine a patient health status or patient health status trend.

Figure 13:
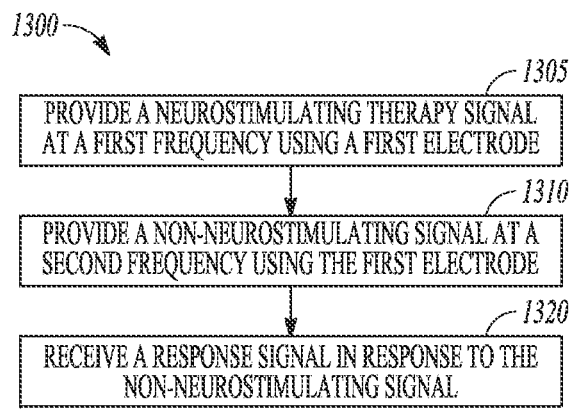
FIG. 13 illustrates generally an example that can include providing neurostimulating and non-neurostimulation signals to a patient body.

FIG. 13 illustrates generally an example that can include providing a neurostimulating therapy signal and a non-neurostimulating signal. At 1305, a neurostimulating therapy signal can be provided at a first frequency using at least a first electrode. For example, the neurostimulating therapy signal can include an autonomic modulation therapy signal, such as can be delivered to the vagus nerve 103 using the first electrode 111. The neurostimulating therapy signal can be a biphasic therapy signal having an initial positive phase amplitude of about 100-4000 µA and a positive phase pulse width of about 300 µs. The signal can have a negative phase amplitude of less than about 4000 µA, and can have a recharge portion lasting several milliseconds. The neurostimulating therapy signal provided at 1305 can have a first frequency, such as about 20 Hz, and can be delivered in burst fashion, such as about 5 seconds on and 25 seconds off.

At 1310, a non-neurostimulating signal can be provided at a second frequency, such as at a different frequency than the first frequency. The non-neurostimulating signal can be an electrical test signal, such as the impedance plethysmography signal pulse 700. The signal can be appended to or incorporated with the neurostimulating therapy signal provided at 1305, such as according to the discussion of FIG. 8, 9, or 10, among other techniques. The non-neurostimulating signal can be a sub-capture threshold signal, such as having a relatively low signal amplitude or narrow pulse width. In an example, the non-neurostimulating signal can have an amplitude of about 100 µA and a puke width of about 40 µs. The signal can be provided at a second frequency, such as about 10 Hz. In an example, the non-neurostimulating signal can be continuously delivered, such as independently of the burst delivery of the neurostimulating signal provided at 1305.

At 1320, an electrical response signal can be received, such as in response to the non-neurostimulating signal. For example, the electrical response signal can be a voltage signal, a current signal, or an impedance signal that can be received using the detector circuit 222. In an example, the received signal can be passed to the processor circuit 110 or the external module 115 and plethysmography techniques can be used to analyze the received impedance signal, such as to determine a patient physiological status. For example, impedance plethysmography can be used to determine a dimension of a portion of an internal organ or blood vessel in the subject body 101.

The electrical response signal can be received at 1320, such as almost immediately after the non-neurostimulating signal is provided at 1310. In an example, the amplitude or shape of the neurostimulating signal provided at 1305 can influence when or how the electrical response signal is received at 1320.

Figure 14:
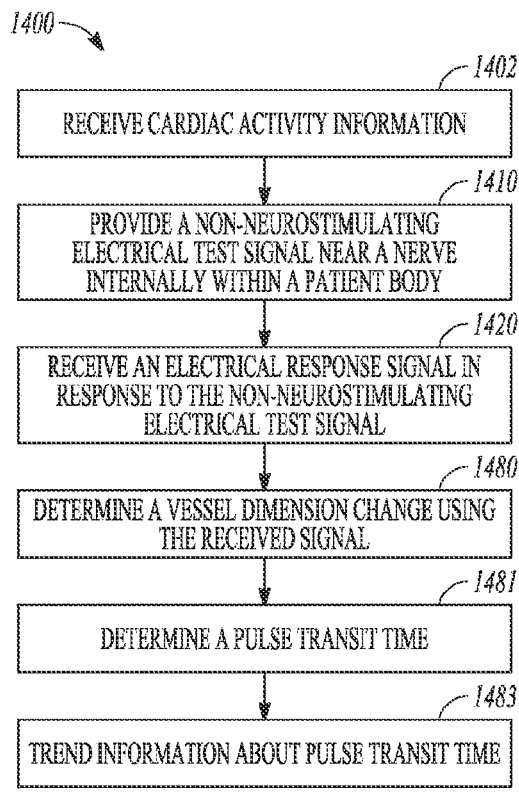
FIG. 14 illustrates generally an example that can include trending information about a pulse transit time.

FIG. 14 illustrates generally an example that can include trending information about a pulse transit time. At 1402, cardiac activity information can be received by the processor circuit 110. Cardiac activity information can include, among other things, an ECG signal, a heart sound signal, or information from the physiological sensor 204 that can be used to determine cardiac activity or identify a portion of a cardiac cycle. Timing information can be associated with the cardiac activity information. For example, a time $t_1$ can be associated with, among other events, a local minimum of a QRS wave for a single cardiac cycle or an emptying of a left ventricle of the heart.

At 1410, a non-neurostimulating electrical signal, such as a test signal, can be provided to the subject body 101, such as near nerve tissue. In an example, the non-neurostimulating electrical signal can be provided according to the discussion at 1310. The non-neurostimulating electrical signal can be a pulse signal, such as a biphasic pulse signal, with an amplitude and pulse width below a nerve tissue capture threshold. At 1420, an electrical response signal can be received in response to the non-neurostimulation electrical signal. The response signal can be received using the detector circuit 222, such as according to the discussion at 1220.

At 1480, a blood vessel dimension change can be determined using the received electrical response signal. For example, the blood vessel dimension change can be determined according to the discussion at 1180. A time $t_2$ can be associated with the blood vessel dimension change, such as to indicate when the blood vessel dimension change exceeds a particular dimension change threshold. The dimension of the blood vessel can change for various reasons, such as in response to a pulse blood pressure wave of blood flowing through a cross-section of the vessel. Depending on the sampling rate of the detector circuit 222, the time $t_2$ can indicate different portions of the arrival or departure of the pulse blood pressure wave. At sufficiently high sampling rates, the detector circuit 222 and the processor circuit 110 can be used to continuously monitor a blood vessel dimension change, such as a radial dimension change of the carotid artery 104. In an example, local relative maxima and minima of a pulse pressure wave can be determined.

At 1481, a pulse transit time can be determined. For example, the detector circuit 222 can receive an electrical response signal at time $t_2$ that can indicate an arrival or presence of a pulse blood pressure wave in a portion of a blood vessel, such as in a cervical region of the carotid artery 104 near the first electrode 111. The pulse transit time can be calculated as the difference in time between $t_2$ and $t_1$. In an example, the pulse transit time can indicate the interval of time between the emptying of the left ventricle of the heart and the arrival of the pulse blood pressure wave at a cervical location in the subject body 101.

In an example, electrical response signals can be received at several locations along a blood vessel, such as along the carotid artery 104, to monitor the progression of the blood pressure wave. By obtaining multiple response signals along a length of the carotid artery 104, the effects of axial strain can be monitored concurrently with pulse transit time to obtain an improved determination of arterial compliance.

At 1483, pulse transit time information can be trended. Trending pulse transit time information can provide information about a patient health status such as over the course of a day or multiple days. For example, a patient's pulse transit time can be monitored over a period of several weeks or months to monitor changes in arterial compliance. In an example, a decrease in arterial compliance can indicate an increase in pulse pressure and a decrease in stroke volume. Such changes can be used to indicate a patient health status.

Figure 15:
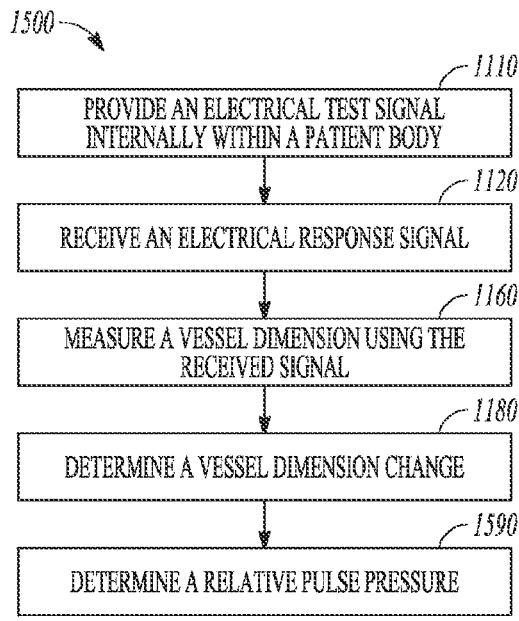
FIG. 15 illustrates generally an example that can include determining a relative pulse pressure.

FIG. 15 illustrates generally an example that can include determining a relative pulse pressure. The example of FIG. 15 can include providing an electrical test signal internally within a patient body, such as according to the discussion at 1110; receiving an electrical response signal, such as according to the discussion at 1120; measuring a vessel dimension using the received signal, such as according to the discussion at 1160; or determining a vessel dimension change, such as according to the discussion at 1180.

At 1590, a relative pulse pressure can be determined, such as using the received electrical response signal or the determined vessel dimension change. For example, a relative pulse pressure can be determined using impedance plethysmography techniques and the received electrical response signal. A pulse pressure can be measured as a difference between a maximum vessel impedance and a minimum vessel impedance because vessel impedance can be correlated to vessel pressure (see, for example the discussion of FIG. 5).

In an example, a pulse pressure determined using vessel impedance information can be correlated with an actual pressure in a blood vessel, such as where a blood pressure sensor is available to provide information concurrently with the received electrical response signal. In an example, the pulse pressure can be a relative pressure, such as can be compared to other pulse pressure measurements taken from the same subject body 101, such as over multiple cardiac cycles. For example, a patient's pulse pressure can be determined at first and second times according to the discussion of FIG. 5, and the pulse pressures can be compared to provide an indication of a patient health status in an example, $\Delta p_1$ can correspond to a relative pulse pressure measurement taken on a first day, and $\Delta p_2$ can correspond to a relative pulse pressure measurement taken on a different second day. The two relative pulse pressures can be trended or otherwise compared to provide a patient health status.

VARIOUS NOTES & EXAMPLES

Example 1 includes subject matter (such as an apparatus) comprising an electrical energy delivery circuit configured to provide an electrical test signal to a location internal to a patient body and near a blood vessel, a detector circuit configured to receive an electrical response signal in response to the electrical test signal, and a signal processor circuit, coupled to the electrical energy delivery circuit and the detector circuit. In Example 1, the signal processor circuit can be configured to determine a vessel dimension using the received response signal, compare the determined vessel dimension to a reference vessel dimension to determine a vessel dimension change, or output information about a vessel dimension change.

In Example 2, the subject matter of Example 1 can optionally include an electrical energy delivery circuit that is configured to provide the electrical test signal using an electrode disposed in a cervical region near a carotid artery and a vagus nerve.

In Example 3, the subject matter of one or any combination of Examples 1-2 can optionally include an electrical energy delivery circuit that is configured to provide an electrical test signal as a non-neurostimulating electrical test signal.

In Example 4, the subject matter of one or any combination of Examples 1-3 can optionally include an electrical energy delivery circuit that is configured to provide a series of non-neurostimulating electrical test signals. In Example 4, the detector circuit can be configured to receive a corresponding series of electrical response signals in response to a series of non-neurostimulating electrical test signals, and the signal processor circuit can be configured to determine a vessel dimension change using the series of received electrical response signals.

In Example 5, the subject matter of one or any combination of Examples 1-4 can optionally include an electrode, and the electrical energy delivery circuit is configured to provide a neurostimulating therapy signal to the electrode, and the electrical energy delivery circuit is further configured to provide a non-neurostimulating test signal to the same electrode.

In Example 6, the subject matter of one or any combination of Examples 1-5 can optionally include an electrical energy delivery circuit that is configured to provide a neurostimulating therapy signal at a first frequency, and to provide an electrical test signal at a different second frequency.

In Example 7, the subject matter of one or any combination of Examples 1-6 can optionally include an electrical energy delivery circuit that is configured to provide a neurostimulating therapy signal to a vagus nerve, and is configured to provide an electrical test signal as a portion of the neurostimulating therapy signal.

In Example 8, the subject matter of one or any combination of Examples 1-7 can optionally include an electrical energy delivery circuit that is configured to provide an autonomic modulation therapy signal to a vagus nerve.

In Example 9, the subject matter of one or any combination of Examples 1-8 can optionally include an electrical energy delivery circuit that is configured to provide a first neurostimulating therapy signal pulse phase and a second non-neurostimulating signal pulse phase.

In Example 10, the subject matter of one or any combination of Examples 1-9 can optionally include a signal processor circuit that is configured to determine a pulse transit time using information about a vessel dimension change, and output information about a patient health status using the pulse transit time.

In Example 11, the subject matter of Example 10 can optionally include the signal processor circuit, which can be further configured to determine the pulse transit time using a temporal reference indication received from at least one of a heart sound signal or an electrocardiograph signal.

In Example 12, the subject matter of one or any combination of Examples 10-11 can optionally include the signal processor circuit, which can be further configured to trend the pulse transit time over multiple cardiac cycles, and output information about a patient health status using information about the trended pulse transit time.

In Example 13, the subject matter of one or any combination of Examples 1-12 can optionally include a signal processor circuit that is configured to determine a relative pulse pressure using information about a vessel dimension change, and output information about a patient health status using the relative pulse pressure.

In Example 14, the subject matter of Example 13 can optionally include the signal processor circuit, which can be configured to trend the relative pulse pressure over multiple cardiac cycles, and output information about a patient health status using information about the trended relative pulse pressure.

In Example 15, the subject matter of one or any combination of Examples 1-14 can optionally include a signal processor circuit that is configured to determine at least one of an arterial compliance, an autonomic status, a cardiac contractility, a pulmonary vein distension, a respiratory effort, a respiratory disturbance, or a fluid status using a determined change in the vessel dimension. In Example 15, the signal processor circuit can be configured to output information about a patient health status using the at least one of an arterial compliance, an autonomic status, a cardiac contractility, a pulmonary vein distension, a respiratory effort, a respiratory disturbance, or a fluid status.

In Example 16, the subject matter of one or any combination of Examples 1-15 can optionally include a signal processor circuit that is configured to determine a radial vessel dimension change of a blood vessel.

In Example 17, the subject matter of one or any combination of Examples 1-16 can optionally include an electrical energy delivery circuit that is configured to provide the electrical test signal in response to a signal provided by a physiological sensor comprising at least one of a posture sensor, a heart rate sensor, a respiration rate sensor, a respiratory phase sensor, a patient physical activity level sensor, or an arrhythmia sensor.

In Example 18, the subject matter of one or any combination of Examples 1-17 can optionally include a signal processor that is configured to provide output information in response to a signal provided by a physiological sensor comprising at least one of a posture sensor, a heart rate sensor, a respiration rate sensor, a respiratory phase sensor, a patient physical activity level sensor, or an arrhythmia sensor.

Example 19 can include, or can optionally be combined with the subject matter of one or any combination of Examples 1-18 to include, subject matter (such as a method, a means for performing acts, or a processor-readable medium including instructions that, when performed by the processor, cause the processor to perform acts) comprising using a previously implanted electrode, providing an electrical test signal internally within a patient body and near a blood vessel, receiving an electrical response signal in response to the electrical test signal, measuring a vessel dimension using the received response signal, comparing the measured vessel dimension to a reference vessel dimension to determine a vessel dimension change, and outputting information about the vessel dimension change.

In Example 20, the subject matter of Example 19 can optionally comprise providing an electrical test signal in a cervical region near a carotid artery and a vagus nerve.

In Example 21, the subject matter of one or any combination of Examples 19-20 can optionally comprise providing an electrical test signal as a non-neurostimulating signal using a previously implanted electrode.

In Example 22, the subject matter of Example 21 can optionally comprise providing a series of non-neurostimulating signals to the vagus nerve, receiving a corresponding series of electrical response signals in response to the series of non-neurostimulating signals, and measuring a vessel dimension using the series of received electrical response signals.

In Example 23, the subject matter of one or any combination of Examples 19-22 can optionally comprise providing a neurostimulating therapy signal at a first frequency to a vagus nerve using a previously implanted electrode, and providing an electrical test signal at a different second frequency using the previously implanted electrode.

In Example 24, the subject matter of one or any combination of Examples 19-23 can optionally comprise providing a neurostimulating therapy signal to a vagus nerve using a previously implanted electrode, and providing an electrical test signal as a portion of the neurostimulating therapy signal using a previously implanted electrode. Example 24 can optionally comprise providing a series of neurostimulating therapy signals to a vagus nerve using the previously implanted electrode, and providing a series of electrical test signals that correspond with the series of neurostimulating therapy signals.

In Example 25, the subject matter of Example 24 can optionally comprise providing an autonomic modulation therapy signal to the vagus nerve.

In Example 26, the subject matter of one or any combination of Examples 19-25 can optionally comprise providing a neurostimulating therapy signal pulse phase and a non-neurostimulating signal pulse phase.

In Example 27, the subject matter of one or any combination of Examples 19-26 can optionally comprise determining a pulse transit time using information about a vessel dimension change, and outputting information about a patient health status using the pulse transit time.

In Example 28, the subject matter of Example 27 can optionally comprise determining a pulse transit time using a portion of an electrocardiograph signal or a heart sound signal to provide a temporal reference.

In Example 29, the subject matter of one or any combination of Examples 27-28 can optionally comprise trending a pulse transit time over multiple cardiac cycles. Example 29 can optionally comprise outputting information about a patient health status using the trended pulse transit time.

In Example 30, the subject matter of one or any combination of Examples 19-29 can optionally comprise determining a relative pulse pressure using information about a vessel dimension change, and outputting information about a patient health status using the relative pulse pressure.

In Example 31, the subject matter of one or any combination of Examples 19-30 can optionally comprise providing an electrical test signal in response to a signal provided by a physiological sensor comprising at least one of a posture sensor, a heart rate sensor, a respiration rate sensor, a respiratory phase sensor, a patient physical activity level sensor, or an arrhythmia sensor.

In Example 32, the subject matter of one or any combination of Examples 19-31 can optionally comprise outputting information in response to a signal provided by a physiological sensor comprising at least one of a posture sensor, a heart rate sensor, a respiration rate sensor, a respiratory phase sensor, a patient physical activity level sensor, or an arrhythmia sensor.

In Example 33, the subject matter of one or any combination of Examples 1-32 can optionally comprise an electrical energy delivery circuit configured to provide a non-neurostimulating electrical test signal using an electrode disposed in a cervical region near a carotid artery and a vagus nerve. Example 33 can optionally comprise a detector circuit, such as configured to receive an electrical response signal in response to the non-neurostimulating electrical test signal, and a signal processor circuit, coupled to the electrical energy delivery circuit and the detector circuit. The signal processor circuit can be configured to, among other things, determine a radial blood vessel dimension using the received response signal, compare the determined radial blood vessel dimension to a reference radial blood vessel dimension to determine a radial blood vessel dimension change, determine at least one of a pulse transit time or a relative pulse pressure using information about the radial blood vessel dimension change, or output information about a patient health status using the at least one of the puke transit time or the relative pulse pressure.

In Example 34, the subject matter of one or any combination of Examples 1-33 can optionally comprise Obtaining reference vessel dimension information, such as during a calibration mode or learning period. Example 34 can include receiving information about a vessel dimension, such as using plethysmography, imaging, or other techniques, such as over one or more patient physiological cycles, and determining a reference vessel dimension using the information about the vessel dimension.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents incorporated by reference, the usage in this document controls.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(h), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus, comprising:
    an electrode configured to be extravascularly implanted, the extravascularly-implanted electrode adapted for encircling extravascular nerve tissue near a blood vessel without encircling the blood vessel;
    an electrical energy delivery circuit configured to be coupled to the extravascularly-implanted electrode and configured to:
        provide an electrical test signal directed from the extravascularly-implanted electrode to a location internal to a patient body and near the blood vessel when the electrode encircles the extravascular nerve tissue without encircling the blood vessel; and
        provide an electrostimulation signal directed from the extravascularly-implanted electrode toward the extravascular nerve tissue when the electrode encircles the extravascular nerve tissue without encircling the blood vessel;
    a detector circuit configured to receive an electrical response signal in response to the electrical test signal; and
    a signal processor circuit, coupled to the electrical energy delivery circuit and the detector circuit, the signal processor circuit configured to:
        determine a vessel dimension of the blood vessel near the extravascularly-implanted electrode using the received electrical response signal;
        compare the determined vessel dimension to a reference vessel dimension to determine a vessel dimension change; and
        output an indication of the determined vessel dimension change.

2. The apparatus of claim 1, wherein the electrical energy delivery circuit is configured to provide the electrical test signal to the extravascular nerve tissue, wherein the extravascular nerve tissue includes a vagus nerve in a cervical region near the blood vessel including a carotid artery.

3. The apparatus of claim 2, wherein the electrical energy delivery circuit is configured to provide the electrical test signal as a non-neurostimulating electrical test signal.

4. The apparatus of claim 2, wherein the electrical energy delivery circuit is configured to provide a series of non-neurostimulating electrical test signals;
    wherein the detector circuit is configured to receive a corresponding series of electrical response signals in response to the series of non-neurostimulating electrical test signals; and
    wherein the signal processor circuit is configured to determine the vessel dimension change of the blood vessel near the extravascularly-implanted electrode using the series of received electrical response signals.

5. The apparatus of claim 1, further comprising an electrode;
    wherein the electrical energy delivery circuit is configured to provide a neurostimulating therapy signal to the electrode; and
    wherein the electrical energy delivery circuit is further configured to provide a non-neurostimulating test signal to the same electrode.

6. The apparatus of claim 1, wherein the electrical energy delivery circuit is configured to provide a neurostimulating therapy signal directed from the extravascularly-implanted electrode toward a vagus nerve; and
    wherein the electrical energy delivery circuit is configured to provide the electrical test signal as a portion of the neurostimulating therapy signal.

7. The apparatus of claim 1, wherein the electrical energy delivery circuit is configured to provide a signal waveform comprising a first neurostimulating therapy signal pulse phase and a second non-neurostimulating signal pulse phase incapable of stimulating the nerve tissue.

8. The apparatus of claim 1, wherein the signal processor circuit is further configured to:
    determine a pulse transit time using information about the vessel dimension change; and
    output information about a patient health status using the pulse transit time.

9. The apparatus of claim 8, wherein the signal processor circuit is further configured to:
    trend the pulse transit time over multiple cardiac cycles; and
    output the information about a patient health status using information about the trended pulse transit time.

10. The apparatus of claim 1, wherein the signal processor circuit is further configured to:
    determine a relative pulse pressure using information about the vessel dimension change; and
    output information about a patient health status using the relative pulse pressure.

11. The apparatus of claim 10, wherein the signal processor circuit is further configured to:
    trend the relative pulse pressure over multiple cardiac cycles; and
    output the information about a patient health status using information about the trended relative pulse pressure.

12. The apparatus of claim 1, wherein the signal processor circuit is further configured to determine at least one of an arterial compliance, an autonomic status, a cardiac contractility, a pulmonary vein distension, a respiratory effort, a respiratory disturbance, or a fluid status using the determined change in the vessel dimension; and
    output information about a patient health status using the at least one of an arterial compliance, an autonomic status, a cardiac contractility, a pulmonary vein distension, a respiratory effort, a respiratory disturbance, or a fluid status.

13. The apparatus of claim 1, wherein the signal processor circuit is configured to determine a radial vessel dimension change of the blood vessel.

14. The apparatus of claim 1, wherein the electrical energy delivery circuit is configured to provide the electrical test signal in response to a signal provided by a physiological sensor comprising at least one of:
- a posture sensor;
- a heart rate sensor;
- a respiration rate sensor;
- a respiratory phase sensor;
- a patient physical activity level sensor;
- or an arrhythmia sensor.

15. The apparatus of claim 1, wherein the signal processor circuit is configured to provide the output indication in response to a signal provided by a physiological sensor comprising at least one of:
- a posture sensor;
- a heart rate sensor;
- a respiration rate sensor;
- a respiratory phase sensor;
- a patient physical activity level sensor;
- or an arrhythmia sensor.

16. A method of using an extravascularly-implanted electrode positioned at an extravascular nerve tissue, the method comprising:
providing an electrical test signal directed from the extravascularly-implanted electrode to a location internal to a patient body and near a blood vessel, the extravascularly-implanted electrode encircling the extravascular nerve tissue without encircling the blood vessel;
receiving an electrical response signal in response to the electrical test signal;
measuring, using a processor circuit, a vessel dimension of the blood vessel near the extravascularly-implanted electrode using the received electrical response signal;
comparing, using a processor circuit, the measured vessel dimension to a reference vessel dimension to determine a vessel dimension change;
outputting an indication of the determined vessel dimension change; and
providing an electrostimulation signal directed from the extravascularly-implanted electrode toward the extravascular nerve tissue.

17. The method of claim 16, wherein the providing the electrical test signal includes providing the electrical test signal to the extravascular nerve tissue, wherein the extravascular nerve tissue includes a vagus nerve in a cervical region near the blood vessel including a carotid artery.

18. The method of claim 16, further comprising:
providing a neurostimulating therapy signal directed from the extravascularly-implanted electrode to a vagus nerve; and
providing the electrical test signal as a portion of the neurostimulating therapy signal.

19. The method of claim 16, further comprising:
determining at least one of a pulse transit time or a relative pulse pressure using the information about the vessel dimension change; and
outputting information about a patient health status using the at least one of the pulse transit time or the relative pulse pressure.

20. An apparatus, comprising:
an electrode configured to be extravascularly implanted in a cervical region, the extravascularly-implanted electrode adapted for encircling a vagus nerve near a carotid artery without encircling the carotid artery;
an electrical energy delivery circuit configured to be coupled to the extravascularly-implanted electrode and configured to:
provide a non-neurostimulating electrical test signal using the extravascularly-implanted electrode when the electrode encircles the vagus nerve without encircling the carotid artery; and
provide a neurostimulating signal directed from the extravascularly-implanted electrode toward the vagus nerve when the electrode encircles the vagus nerve without encircling the carotid artery;
a detector circuit configured to receive an electrical response signal in response to the non-neurostimulating electrical test signal; and
a signal processor circuit, coupled to the electrical energy delivery circuit and the detector circuit, the signal processor circuit configured to:
determine a radial blood vessel dimension of the carotid artery near the extravascularly-implanted electrode using the received electrical response signal;
compare the determined radial blood vessel dimension to a reference radial blood vessel dimension to determine a radial blood vessel dimension change;
determine at least one of a pulse transit time or a relative pulse pressure using information about the radial blood vessel dimension change; and
output information about a patient health status using the at least one of the pulse transit time or the relative pulse pressure.

* * * * *